(12) United States Patent
Bruce et al.

(10) Patent No.: US 9,700,689 B2
(45) Date of Patent: Jul. 11, 2017

(54) MEDICATION DELIVERY APPARATUS AND SYSTEM AND METHODS FOR THE USE AND ASSEMBLY THEREOF

(71) Applicants: Sarah Bruce, Waterloo (CA); James N. Schmidt, London (CA)

(72) Inventors: Sarah Bruce, Waterloo (CA); James N. Schmidt, London (CA)

(73) Assignee: Trudell Medical International, London (CA)

( * ) Notice: Subject to any disclaimer, the term of this patent is extended or adjusted under 35 U.S.C. 154(b) by 720 days.

(21) Appl. No.: 14/030,690

(22) Filed: Sep. 18, 2013

(65) Prior Publication Data
US 2014/0116436 A1 May 1, 2014

Related U.S. Application Data

(63) Continuation of application No. 13/313,876, filed on Dec. 7, 2011, now Pat. No. 8,550,067, which is a
(Continued)

(51) Int. Cl.
*A61M 15/00* (2006.01)
*A61M 16/06* (2006.01)
(Continued)

(52) U.S. Cl.
CPC ...... *A61M 15/009* (2013.01); *A61M 15/0016* (2014.02); *A61M 15/0018* (2014.02);
(Continued)

(58) Field of Classification Search
CPC .......... A61M 15/0016; A61M 15/0018; A61M 15/0026; A61M 15/0086; A61M 15/009;
(Continued)

(56) References Cited

U.S. PATENT DOCUMENTS

| 393,869 A | 12/1888 | Warren |
|---|---|---|
| 2,535,844 A | 12/1950 | Emerson |

(Continued)

FOREIGN PATENT DOCUMENTS

| AU | B-29969/89 | 8/1990 |
|---|---|---|
| CA | 2064860 A1 | 2/1991 |

(Continued)

OTHER PUBLICATIONS

Andersen, J.B. et al., "A new Mode of Administration of Nebulized Bronchodilator in Severe Bronchospasm", Eur. J. Respir Dis Suppl 119, vol. 63, 1982, pp. 97-100.
(Continued)

*Primary Examiner* — Annette Dixon
(74) *Attorney, Agent, or Firm* — Brinks Gilson & Lione

(57) ABSTRACT

A delivery system includes a holding chamber with first, second and third openings, and independently moveable first, second and third flow control members. A delivery system includes a holding chamber and a flow control member including a flap pivotable from an at rest position in a direction toward an outlet of a user interface and away from an output end of the holding chamber in response to a pressure being applied thereto.

27 Claims, 11 Drawing Sheets

Related U.S. Application Data continuation of application No. 11/712,547, filed on Feb. 28, 2007, now Pat. No. 8,074,642, which is a continuation of application No. 11/130,808, filed on May 17, 2005, now Pat. No. 7,201,165, which is a continuation of application No. 10/431,325, filed on May 7, 2003, now Pat. No. 6,904,908.

(60) Provisional application No. 60/382,227, filed on May 21, 2002.

(51) Int. Cl.
  *A61M 16/20* (2006.01)
  *A61M 16/14* (2006.01)

(52) U.S. Cl.
  CPC ........ *A61M 15/0086* (2013.01); *A61M 16/06* (2013.01); *A61M 16/14* (2013.01); *A61M 16/208* (2013.01); *A61M 2205/583* (2013.01); *A61M 2207/00* (2013.01); *Y10T 29/49826* (2015.01)

(58) Field of Classification Search
  CPC ............ A61M 16/06; A61M 2205/183; A61M 2205/44; A61M 2205/581; A61M 11/001; A61M 11/002; A61M 11/06; A61M 15/00; A61M 15/0015; A61M 15/002; A61M 15/0021; A61M 15/0028; A61M 15/0033; A61M 15/0065; A61M 15/0075; A61M 15/008; A61M 15/0091; A61M 15/0093; A61M 15/0098; A61M 16/00; A61M 16/0006; A61M 16/0078; A61M 16/0084; A61M 16/0488; A61M 16/0666; A61M 16/08; A61M 16/0866; A61M 16/10; A61M 16/105; A61M 16/1065; A61M 16/107; A61M 16/127; A61M 16/20; A61M 16/205; A61M 16/206; A61M 16/208; A61M 16/209; A61M 2016/0024; A61M 2016/0027; A61M 2016/003; A61M 2016/0413
  USPC ............ 128/200.14, 200.18, 200.23, 203.23, 128/203.24, 203.29, 205.23, 205.24, 128/206.24, 207.12
  See application file for complete search history.

(56) References Cited

U.S. PATENT DOCUMENTS

| | | | |
|---|---|---|---|
| 2,670,739 A | 3/1954 | McNeill | |
| 2,882,026 A | 4/1959 | Eichelman | |
| 2,951,644 A | 9/1960 | Mahon et al. | |
| 3,172,406 A | 3/1965 | Bird et al. | |
| 3,236,458 A | 2/1966 | Ramis | |
| 3,269,665 A | 8/1966 | Cheney | |
| 3,363,833 A | 1/1968 | Laerdal | |
| 3,467,092 A | 9/1969 | Bird et al. | |
| 3,490,697 A | 1/1970 | Best, Jr. | |
| 3,556,122 A | 1/1971 | Laerdal | |
| 3,565,071 A | 2/1971 | Cobb et al. | |
| 3,580,249 A | 5/1971 | Takaoka | |
| 3,584,621 A | 6/1971 | Bird et al. | |
| 3,630,196 A | 12/1971 | Bird et al. | |
| 3,643,686 A | 2/1972 | Koegel | |
| 3,658,059 A | 4/1972 | Steil | |
| 3,664,337 A | 5/1972 | Lindsey et al. | |
| 3,809,084 A | 5/1974 | Hansen | |
| 3,809,294 A | 5/1974 | Torgenson | |
| 3,826,255 A | 7/1974 | Havstad et al. | |
| 3,838,686 A | 10/1974 | Szekely | |
| 3,874,379 A | 4/1975 | Enfield et al. | |
| 3,896,101 A | 7/1975 | McIntosh et al. | |
| 3,897,779 A | 8/1975 | Hansen | |
| 3,903,884 A | 9/1975 | Huston et al. | |
| 3,990,442 A | 11/1976 | Patneau | |
| 3,994,421 A | 11/1976 | Hansen | |
| 4,081,233 A | 3/1978 | Kitajima et al. | |
| 4,093,124 A | 6/1978 | Morane et al. | |
| 4,094,317 A | 6/1978 | Wasnich | |
| 4,106,503 A | 8/1978 | Rosenthal et al. | |
| 4,116,387 A | 9/1978 | Kremer, Jr. et al. | |
| 4,139,128 A | 2/1979 | Ewald | |
| 4,150,071 A | 4/1979 | Pecina | |
| 4,165,961 A | 8/1979 | Yamamoto et al. | |
| 4,174,712 A | 11/1979 | Moren et al. | |
| 4,182,366 A | 1/1980 | Boehringer | |
| 4,183,361 A | 1/1980 | Russo | |
| 4,198,969 A | 4/1980 | Virag | |
| 4,206,644 A | 6/1980 | Platt | |
| 4,210,140 A | 7/1980 | James et al. | |
| 4,210,155 A | 7/1980 | Grimes | |
| 4,231,375 A | 11/1980 | Boehringer et al. | |
| 4,251,033 A | 2/1981 | Rich et al. | |
| 4,253,468 A | 3/1981 | Lehmbeck | |
| 4,267,832 A | 5/1981 | Hakkinen | |
| 4,268,460 A | 5/1981 | Boiarski et al. | |
| 4,275,722 A | 6/1981 | Sorensen | |
| 4,291,688 A | 9/1981 | Kistler | |
| 4,292,966 A | 10/1981 | Mono et al. | |
| 4,298,023 A | 11/1981 | McGinnis | |
| 4,333,450 A | 6/1982 | Lester | |
| 4,344,573 A | 8/1982 | De Felice | |
| 4,413,784 A | 11/1983 | Dea | |
| 4,429,835 A | 2/1984 | Brugger et al. | |
| 4,452,239 A | 6/1984 | Malem | |
| 4,456,179 A | 6/1984 | Kremer | |
| 4,470,412 A | 9/1984 | Nowacki et al. | |
| 4,484,577 A | 11/1984 | Sackner et al. | |
| 4,496,086 A | 1/1985 | Duchadeau | |
| 4,507,118 A | 3/1985 | Dent | |
| 4,508,118 A | 4/1985 | Toth | |
| 4,509,515 A | 4/1985 | Altounyan et al. | |
| 4,509,688 A | 4/1985 | Gagne et al. | |
| 4,533,082 A | 8/1985 | Maehara et al. | |
| 4,588,129 A | 5/1986 | Shanks | |
| 4,620,670 A | 11/1986 | Hughes | |
| 4,622,968 A | 11/1986 | Persson | |
| 4,627,432 A | 12/1986 | Newell et al. | |
| 4,635,631 A | 1/1987 | Izumi | |
| 4,637,528 A | 1/1987 | Wachinski et al. | |
| 4,641,644 A | 2/1987 | Andersson et al. | |
| 4,646,644 A | 3/1987 | Richmond et al. | |
| 4,657,007 A | 4/1987 | Carlin et al. | |
| 4,674,491 A | 6/1987 | Brugger et al. | |
| 4,677,975 A | 7/1987 | Edgar et al. | |
| 4,746,067 A | 5/1988 | Svoboda | |
| 4,758,224 A | 7/1988 | Siposs | |
| 4,770,413 A | 9/1988 | Green | |
| 4,792,097 A | 12/1988 | Kremer, Jr. et al. | |
| 4,796,614 A | 1/1989 | Nowacki et al. | |
| 4,809,692 A | 3/1989 | Nowacki et al. | |
| 4,832,015 A | 5/1989 | Nowacki et al. | |
| 4,834,083 A | 5/1989 | Byram et al. | |
| 4,846,168 A | 7/1989 | Abiko et al. | |
| 4,852,561 A | 8/1989 | Sperry | |
| 4,886,057 A | 12/1989 | Nave | |
| 4,907,583 A | 3/1990 | Wetterlin et al. | |
| 4,911,157 A | 3/1990 | Miller | |
| 4,940,051 A | 7/1990 | Lankinen | |
| 4,981,295 A | 1/1991 | Belman et al. | |
| 4,984,158 A | 1/1991 | Hillsman | |
| 5,012,803 A | 5/1991 | Foley et al. | |
| 5,012,804 A | 5/1991 | Foley et al. | |
| 5,020,527 A | 6/1991 | Dessertine | |
| 5,020,530 A | 6/1991 | Miller | |
| 5,025,628 A * | 6/1991 | Layman | B60T 11/26 60/585 |
| 5,033,463 A | 7/1991 | Cocozza | |
| 5,040,527 A | 8/1991 | Larson et al. | |
| 5,042,467 A * | 8/1991 | Foley | A61M 15/0086 128/200.14 |

(56) References Cited

U.S. PATENT DOCUMENTS

| | | |
|---|---|---|
| 5,048,729 A | 9/1991 | Pritchard |
| 5,054,477 A | 10/1991 | Terada et al. |
| 5,054,478 A | 10/1991 | Grychowski et al. |
| 5,078,131 A | 1/1992 | Foley |
| 5,086,765 A | 2/1992 | Levine |
| 5,109,840 A | 5/1992 | Daleiden |
| 5,165,392 A | 11/1992 | Small |
| 5,167,506 A | 12/1992 | Kilis et al. |
| 5,170,782 A | 12/1992 | Kocinski |
| 5,178,138 A | 1/1993 | Walstrom et al. |
| 5,193,529 A | 3/1993 | Labaere |
| 5,241,954 A | 9/1993 | Glenn |
| 5,250,287 A | 10/1993 | Cocozza |
| 5,277,175 A | 1/1994 | Riggs et al. |
| 5,280,784 A | 1/1994 | Kohler |
| 5,297,543 A | 3/1994 | Larson et al. |
| 5,299,565 A | 4/1994 | Brown |
| 5,301,662 A | 4/1994 | Bagwell et al. |
| 5,301,663 A | 4/1994 | Small, Jr. |
| 5,309,900 A | 5/1994 | Knoch et al. |
| 5,312,046 A | 5/1994 | Knoch et al. |
| 5,312,281 A | 5/1994 | Takahashi et al. |
| 5,318,015 A | 6/1994 | Mansson et al. |
| 5,333,106 A | 7/1994 | Lanpher et al. |
| 5,337,926 A | 8/1994 | Drobish et al. |
| 5,349,947 A | 9/1994 | Newhouse et al. |
| 5,357,951 A | 10/1994 | Ratner |
| 5,363,842 A | 11/1994 | Mishelevich et al. |
| 355,029 A | 1/1995 | Kinneir et al. |
| 5,383,470 A | 1/1995 | Kolbly |
| 5,385,140 A | 1/1995 | Smith |
| 5,392,648 A | 2/1995 | Robertson |
| 5,398,714 A | 3/1995 | Price |
| 5,427,089 A | 6/1995 | Kraemer |
| 5,431,154 A | 7/1995 | Seigel et al. |
| 5,456,249 A | 10/1995 | Kirk |
| 5,458,136 A | 10/1995 | Jaser et al. |
| 5,461,695 A | 10/1995 | Knoch |
| 5,477,849 A | 12/1995 | Fry |
| 5,479,920 A | 1/1996 | Piper et al. |
| 5,487,378 A | 1/1996 | Robertson et al. |
| 5,497,765 A | 3/1996 | Praud et al. |
| 5,497,872 A | 3/1996 | Pennino |
| 5,501,214 A | 3/1996 | Sabo |
| 5,505,192 A | 4/1996 | Samiotes et al. |
| 5,505,193 A | 4/1996 | Ballini et al. |
| 5,505,194 A | 4/1996 | Adjei et al. |
| 5,511,538 A | 4/1996 | Haber et al. |
| 5,511,539 A | 4/1996 | Lien |
| 5,515,842 A | 5/1996 | Ramseyer et al. |
| 5,518,179 A | 5/1996 | Humberstone et al. |
| 5,520,166 A | 5/1996 | Ritson et al. |
| 5,522,380 A | 6/1996 | Dwork |
| 5,533,497 A | 7/1996 | Ryder |
| 5,533,501 A | 7/1996 | Denyer |
| 5,544,647 A | 8/1996 | Jewett et al. |
| 5,549,102 A | 8/1996 | Lintl et al. |
| 5,562,093 A | 10/1996 | Gerson |
| 5,570,682 A | 11/1996 | Johnson |
| 5,575,282 A | 11/1996 | Knoch et al. |
| 5,582,162 A | 12/1996 | Petersson |
| 5,584,285 A | 12/1996 | Salter et al. |
| 5,596,982 A | 1/1997 | Blaha-Schnabel |
| 5,598,839 A | 2/1997 | Niles et al. |
| 5,613,489 A | 3/1997 | Miller et al. |
| 5,617,844 A | 4/1997 | King |
| 5,622,162 A | 4/1997 | Johansson et al. |
| 5,629,032 A | 5/1997 | Pennino |
| 5,630,409 A | 5/1997 | Bono et al. |
| 5,645,049 A * | 7/1997 | Foley .................... A61M 15/00 128/200.23 |
| 5,647,345 A | 7/1997 | Saul |
| 5,657,853 A | 8/1997 | Pennino |
| 5,657,926 A | 8/1997 | Toda |
| 5,658,221 A | 8/1997 | Hougen |
| 5,676,130 A | 10/1997 | Gupte et al. |
| 5,687,912 A | 11/1997 | Denyer |
| 5,701,886 A | 12/1997 | Ryatt |
| 5,704,344 A | 1/1998 | Cole |
| 5,724,959 A | 3/1998 | McAughey et al. |
| 5,724,962 A | 3/1998 | Vidgren et al. |
| 5,738,087 A | 4/1998 | King |
| 5,740,793 A | 4/1998 | Hodson et al. |
| 5,740,966 A | 4/1998 | Blaha-Schnabel |
| 5,752,505 A | 5/1998 | Ohki et al. |
| 5,755,221 A | 5/1998 | Bisgaard |
| 5,758,638 A | 6/1998 | Kreamer |
| 5,765,553 A | 6/1998 | Richards et al. |
| 5,775,320 A | 7/1998 | Patton et al. |
| 5,792,057 A | 8/1998 | Rubsamen et al. |
| 5,803,078 A | 9/1998 | Brauner |
| 5,816,240 A * | 10/1998 | Komesaroff ...... A61M 15/0086 128/200.14 |
| 5,823,179 A | 10/1998 | Grychowski et al. |
| 5,840,279 A | 11/1998 | Narodylo et al. |
| 5,848,588 A | 12/1998 | Foley et al. |
| 5,848,599 A | 12/1998 | Todd |
| 5,855,202 A | 1/1999 | Andrade |
| 5,865,172 A | 2/1999 | Butler et al. |
| 5,875,774 A | 3/1999 | Clementi et al. |
| 5,881,718 A | 3/1999 | Mortensen et al. |
| 5,890,998 A | 4/1999 | Hougen |
| 5,896,857 A | 4/1999 | Hely et al. |
| 5,899,201 A | 5/1999 | Schultz et al. |
| 5,899,832 A | 5/1999 | Hougen |
| 5,925,831 A | 7/1999 | Storsved |
| 5,937,852 A | 8/1999 | Butler et al. |
| 5,954,049 A | 9/1999 | Foley et al. |
| 5,957,389 A | 9/1999 | Wunderlich et al. |
| 5,988,160 A | 11/1999 | Foley et al. |
| 6,000,394 A | 12/1999 | Blaha-Schnabel et al. |
| 6,026,807 A * | 2/2000 | Puderbaugh ...... A61M 15/0086 128/200.14 |
| 6,026,808 A | 2/2000 | Armer et al. |
| 6,026,809 A | 2/2000 | Abrams et al. |
| 6,039,042 A * | 3/2000 | Sladek .............. A61M 15/0086 128/200.23 |
| 6,044,841 A | 4/2000 | Verdun et al. |
| 6,044,859 A | 4/2000 | Davis |
| 6,073,628 A | 6/2000 | Butler et al. |
| 6,085,741 A | 7/2000 | Becker |
| 6,089,105 A | 7/2000 | Ricciardelli |
| 6,089,225 A | 7/2000 | Brown et al. |
| 6,102,036 A | 8/2000 | Slutsky et al. |
| 6,106,479 A | 8/2000 | Wunderlich |
| 6,116,233 A | 9/2000 | Denyer et al. |
| 6,116,239 A | 9/2000 | Volgyesi |
| 6,123,075 A | 9/2000 | Kirk |
| 6,129,080 A | 10/2000 | Pitcher et al. |
| 6,131,568 A | 10/2000 | Denyer et al. |
| 6,138,673 A | 10/2000 | Shephard |
| 6,176,237 B1 | 1/2001 | Wunderlich et al. |
| 6,179,164 B1 | 1/2001 | Fuchs |
| 6,223,745 B1 | 5/2001 | Hammarlund et al. |
| 6,228,346 B1 | 5/2001 | Zhang et al. |
| 6,237,589 B1 | 5/2001 | Denyer et al. |
| 6,240,917 B1 | 6/2001 | Andrade |
| 6,253,767 B1 | 7/2001 | Mantz |
| 6,257,231 B1 | 7/2001 | Schick et al. |
| 6,293,279 B1 | 9/2001 | Schmidt et al. |
| 6,338,443 B1 | 1/2002 | Piper |
| 6,345,617 B1 | 2/2002 | Engelbreth et al. |
| 6,367,471 B1 | 4/2002 | Genosar et al. |
| 6,412,481 B1 | 7/2002 | Bienvenu et al. |
| 6,435,176 B1 | 8/2002 | Berg et al. |
| 6,435,177 B1 | 8/2002 | Schmidt et al. |
| 6,450,163 B1 | 9/2002 | Blacker et al. |
| 6,464,388 B2 | 10/2002 | Ligouzat |
| 6,481,435 B2 | 11/2002 | Hochrainer et al. |
| 6,481,438 B1 | 11/2002 | Gallem et al. |
| 6,513,519 B2 | 2/2003 | Gallem |
| 6,513,727 B1 | 2/2003 | Jaser |
| 6,514,177 B1 | 2/2003 | Brugger et al. |
| 6,543,448 B1 | 4/2003 | Smith et al. |

(56) References Cited

U.S. PATENT DOCUMENTS

| | | | |
|---|---|---|---|
| 6,557,549 B2 | 5/2003 | Schmidt et al. |
| 6,578,571 B1 | 6/2003 | Watt |
| 6,581,598 B1 | 6/2003 | Foran et al. |
| 6,584,971 B1 | 7/2003 | Denyer et al. |
| 6,595,203 B1 | 7/2003 | Bird |
| 6,606,990 B2 | 8/2003 | Stapleton et al. |
| 6,606,992 B1 | 8/2003 | Schuler et al. |
| 6,612,303 B1 | 9/2003 | Grychowski et al. |
| 6,631,721 B1 | 10/2003 | Salter et al. |
| 6,644,304 B2 | 11/2003 | Grychowski et al. |
| D483,860 S | 12/2003 | Knoch |
| 6,679,250 B2 | 1/2004 | Walker et al. |
| 6,679,251 B1 | 1/2004 | Gallem et al. |
| 6,679,252 B2 | 1/2004 | Sladek |
| 6,698,421 B2 | 3/2004 | Attolini |
| 6,708,688 B1 | 3/2004 | Rubin et al. |
| 6,732,944 B2 | 5/2004 | Litherland et al. |
| 6,748,945 B2 | 6/2004 | Grychowski et al. |
| 6,752,145 B1 | 6/2004 | Bonney et al. |
| 6,823,862 B2 | 11/2004 | McNaughton |
| 6,848,443 B2 | 2/2005 | Schmidt |
| 6,857,427 B2 | 2/2005 | Ziegler et al. |
| 6,883,517 B2 | 4/2005 | Halamish |
| 6,885,684 B2 | 4/2005 | Ichino |
| 6,904,908 B2 | 6/2005 | Bruce et al. |
| 6,908,449 B2 | 6/2005 | Willis et al. |
| 6,929,003 B2 | 8/2005 | Blacker et al. |
| 6,962,151 B1 | 11/2005 | Knoch et al. |
| 6,978,941 B2 | 12/2005 | Litherland et al. |
| 6,983,747 B2 | 1/2006 | Gallem et al. |
| 6,994,083 B2 | 2/2006 | Foley et al. |
| 7,013,896 B2 | 3/2006 | Schmidt |
| 7,022,764 B2 | 4/2006 | Murray |
| 7,036,505 B2 | 5/2006 | Bacon et al. |
| 7,051,731 B1 | 5/2006 | Rogerson |
| 7,059,320 B2 | 6/2006 | Feiner et al. |
| 7,077,126 B2 | 7/2006 | Kummer et al. |
| 7,080,643 B2 | 7/2006 | Grychowski et al. |
| 7,104,463 B2 | 9/2006 | Litherland et al. |
| 7,131,439 B2 | 11/2006 | Blacker et al. |
| 7,131,440 B2 | 11/2006 | Sonntag |
| 7,201,165 B2 | 4/2007 | Bruce et al. |
| 7,204,245 B2 * | 4/2007 | Johnson .......... A61M 15/0086 128/200.14 |
| 7,252,085 B2 | 8/2007 | Kunschir |
| 7,255,106 B2 | 8/2007 | Gallem et al. |
| 7,261,102 B2 | 8/2007 | Barney et al. |
| 7,267,120 B2 | 9/2007 | Rustad et al. |
| 7,270,123 B2 | 9/2007 | Grychowski et al. |
| 7,360,537 B2 | 4/2008 | Snyder et al. |
| 7,404,400 B2 | 7/2008 | Lulla et al. |
| 7,458,372 B2 | 12/2008 | Feiner et al. |
| 7,559,322 B2 | 7/2009 | Foley et al. |
| 7,562,656 B2 | 7/2009 | Gallem et al. |
| 7,568,480 B2 | 8/2009 | Foley et al. |
| 7,634,995 B2 | 12/2009 | Grychowski et al. |
| 7,748,385 B2 | 7/2010 | Lieberman et al. |
| 7,758,886 B2 | 7/2010 | Jauernig et al. |
| 8,074,641 B2 | 12/2011 | Gallem et al. |
| RE43,174 E | 2/2012 | Schmidt et al. |
| 2001/0013341 A1 | 8/2001 | Gallem |
| 2001/0032643 A1 | 10/2001 | Hochrainer et al. |
| 2001/0054421 A1 | 12/2001 | Jaser et al. |
| 2002/0005196 A1 | 1/2002 | Brugger |
| 2002/0020762 A1 | 2/2002 | Selzer et al. |
| 2002/0056448 A1 | 5/2002 | Stapleton et al. |
| 2002/0104531 A1 | 8/2002 | Malone |
| 2002/0157663 A1 | 10/2002 | Blacker et al. |
| 2003/0005929 A1 | 1/2003 | Grychowski et al. |
| 2003/0015193 A1 | 1/2003 | Grychowski et al. |
| 2003/0037785 A1 | 2/2003 | Sonntag |
| 2003/0037788 A1 | 2/2003 | Gallem et al. |
| 2003/0089368 A1 | 5/2003 | Zhao |
| 2003/0136399 A1 | 7/2003 | Foley et al. |
| 2003/0136499 A1 | 7/2003 | Boiteau |
| 2003/0159694 A1 | 8/2003 | McNaughton |
| 2003/0189067 A1 * | 10/2003 | Stull .......... B65D 47/2031 222/494 |
| 2003/0205226 A1 | 11/2003 | Gallem et al. |
| 2003/0226562 A1 | 12/2003 | Schmidt et al. |
| 2004/0031485 A1 | 2/2004 | Rustad et al. |
| 2004/0060556 A1 | 4/2004 | Halamish |
| 2004/0089295 A1 | 5/2004 | Gallum et al. |
| 2004/0094148 A1 | 5/2004 | Lulla et al. |
| 2004/0173209 A1 | 9/2004 | Grychowski et al. |
| 2004/0231665 A1 | 11/2004 | Lieberman et al. |
| 2004/0250816 A1 | 12/2004 | Kummer et al. |
| 2005/0039741 A1 | 2/2005 | Gallem et al. |
| 2005/0056274 A1 | 3/2005 | Kunschir |
| 2005/0183718 A1 | 8/2005 | Wuttke et al. |
| 2005/0205085 A1 | 9/2005 | Blacker et al. |
| 2005/0224076 A1 | 10/2005 | Pfichner et al. |
| 2005/0244339 A1 | 11/2005 | Jauernig et al. |
| 2006/0011196 A2 | 1/2006 | Gallem et al. |
| 2006/0048772 A1 | 3/2006 | Borgschulte |
| 2006/0054166 A1 | 3/2006 | Knoch et al. |
| 2006/0057073 A1 | 3/2006 | Lintz et al. |
| 2006/0065267 A1 | 3/2006 | Tran et al. |
| 2006/0102172 A1 | 5/2006 | Feiner et al. |
| 2006/0102178 A1 | 5/2006 | Feiner et al. |
| 2006/0157052 A1 | 7/2006 | Foley et al. |
| 2006/0162723 A1 | 7/2006 | Selzer et al. |
| 2006/0207591 A1 | 9/2006 | Gallem et al. |
| 2006/0213503 A1 | 9/2006 | Borgschulte et al. |
| 2006/0254578 A1 | 11/2006 | Boehm et al. |
| 2006/0254579 A1 | 11/2006 | Grychowski et al. |
| 2006/0289002 A1 | 12/2006 | Hetzer et al. |
| 2007/0023036 A1 | 2/2007 | Grychowski et al. |
| 2007/0204864 A1 | 9/2007 | Grychowski et al. |
| 2007/0235028 A1 | 10/2007 | Bruce et al. |
| 2008/0083407 A1 | 4/2008 | Grychowski et al. |
| 2008/0257345 A1 | 10/2008 | Snyder et al. |
| 2009/0272820 A1 | 11/2009 | Foley et al. |

FOREIGN PATENT DOCUMENTS

| | | |
|---|---|---|
| CA | 2072544 A1 | 12/1992 |
| CA | 2124519 A1 | 11/1994 |
| DE | 2804852 A1 | 11/1986 |
| DE | 8703534 U1 | 8/1987 |
| DE | 19902847 C1 | 5/2000 |
| DE | 19953317 C1 | 2/2001 |
| EP | 0 009 667 A1 | 4/1980 |
| EP | 0 015 247 B1 | 12/1982 |
| EP | 0 134 847 A1 | 3/1985 |
| EP | 0 281 650 A1 | 9/1988 |
| EP | 0 372 148 A1 | 6/1990 |
| EP | 0 414 536 A2 | 2/1991 |
| EP | 0 289 563 B1 | 5/1991 |
| EP | 0 281 650 B1 | 3/1992 |
| EP | 0 514 085 A1 | 11/1992 |
| EP | 0 520 571 A1 | 12/1992 |
| EP | 0 587 380 A1 | 3/1994 |
| EP | 0 347 779 B1 | 5/1994 |
| EP | 0 475 257 B1 | 6/1994 |
| EP | 0 601 708 A2 | 6/1994 |
| EP | 0 641 570 A1 | 3/1995 |
| EP | 0 678 306 A2 | 10/1995 |
| EP | 0 548 152 B1 | 7/1996 |
| EP | 0 711 609 A3 | 10/1996 |
| EP | 0 514 085 B1 | 7/1997 |
| EP | 0 587 380 B1 | 11/1997 |
| EP | 0 820 780 A1 | 1/1998 |
| EP | 0 520 571 B1 | 9/1998 |
| EP | 0 585 379 B1 | 9/1998 |
| EP | 0 855 224 A2 | 7/1999 |
| EP | 0 855 224 A3 | 7/1999 |
| EP | 0 938 908 A2 | 9/1999 |
| EP | 0 601 708 B1 | 3/2000 |
| EP | 1 358 901 A2 | 11/2003 |
| EP | 0 855 224 B1 | 5/2004 |
| EP | 0 938 906 B1 | 11/2005 |
| FR | 1 070 292 A | 7/1954 |
| FR | 2 763 507 A | 11/1998 |

(56) References Cited

FOREIGN PATENT DOCUMENTS

| | | |
|---|---|---|
| GB | 497530 A | 12/1939 |
| GB | 675524 A | 7/1952 |
| GB | 975754 A | 11/1964 |
| GB | 1017032 A | 1/1966 |
| GB | 2000555 A | 1/1979 |
| GB | 1598081 A | 9/1981 |
| GB | 2253200 A | 9/1992 |
| GB | 2299512 A | 10/1996 |
| GB | 2310607 A | 9/1997 |
| JP | 55-40595 A | 3/1980 |
| JP | 05-048152 U | 6/1993 |
| JP | 06-178954 A | 6/1994 |
| WO | WO 88/03419 A1 | 5/1988 |
| WO | WO 90/09203 A1 | 8/1990 |
| WO | WO 91/00117 A1 | 1/1991 |
| WO | WO 92/20391 A1 | 11/1992 |
| WO | WO 93/11817 A1 | 6/1993 |
| WO | WO 94/17753 A1 | 8/1994 |
| WO | WO 95/20414 A1 | 8/1995 |
| WO | WO 96/32149 A1 | 10/1996 |
| WO | WO 97/01365 A1 | 1/1997 |
| WO | WO 97/31668 A1 | 9/1997 |
| WO | WO 98/19727 A1 | 5/1998 |
| WO | WO 98/26827 A1 | 6/1998 |
| WO | WO 98/26828 A2 | 6/1998 |
| WO | WO 98/41265 A1 | 9/1998 |
| WO | WO 98/44974 A1 | 10/1998 |
| WO | WO 99/16490 A1 | 4/1999 |
| WO | WO 99/40959 A1 | 8/1999 |
| WO | WO 99/53982 A1 | 10/1999 |
| WO | WO 00/27455 A1 | 5/2000 |
| WO | WO 00/59565 A1 | 10/2000 |
| WO | WO 01/76671 A2 | 10/2001 |
| WO | WO 02/04056 A1 | 1/2002 |
| WO | WO 02/05630 A2 | 1/2002 |
| WO | WO 02/24263 A2 | 3/2002 |
| WO | WO 03/053500 A1 | 11/2003 |
| WO | WO 03/097142 A1 | 11/2003 |
| WO | WO 2010/054083 A2 | 5/2010 |

OTHER PUBLICATIONS

Barry, Peter W. et al., "The output of budesonide from spacer devices assessed under simulated breathing conditions," Journal Allergy Clin. Immunol., vol. 104, No. 6, Dec. 1999, pp. 1205-1210.
Callahan, Thomas J., Ph.D., "K981944—BreatheRite," letter from Dept. of Health & Human Services, with enclosure, Aug. 1998, 3 pages.
Frischknecht-Christensen, E.F. et al., "Treatment of Bronchial Asthma with Terbutaline Inhaled by Conespacer Combined With Positive Expiratory Pressure Mask", Chest 100, vol. 2, Aug. 1991, pp. 317-321.
Hickey et al., Aerosol Generation from Propellant-Driven Metered Dose Inhalers, Title and Source Unknown, pp. 417-435.
Mahlmeister, M.J. et al., "Positive-Expiratory-Pressure Mask Therapy: Theoretical and Practical Considerations and a Review of the Literature", Respiratory Care Nov. 1991, vol. 36, No. 11, pp. 1218-1229.
Meeran, K. et al., "Oral and Inhaled Corticosteroids Reduce Bone Formation as Shown by Plasma Osteocalcin Levels", American J. Respir. Crit. Care Med 151:333-336.
Newman, S.P., Aerosol Deposition Consideration in Inhalation Therapy, Chest/88/2/Aug. 1985/ [Supplement], pp. 152s-160s.
Rau, J.L. et al., "Combining a Positive Expiratory Pressure Device with a Metered-Dose Inhaler Reservoir System Using Chlorofluorocarbon Albuterol and Hydrofluoroalkane Albuterol: Effect on Dose and Particle Size Distributions", Respiratory Care, Mar. 2000, vol. 45 No. 3, pp. 320-326.
Rau, J.L., Respiratory Care Pharmacology, 4th ed., Mosby, 2004, pp. 256-261.
Rupperct, L. et al., "Conductive Plastics for Medical Applications," Medical Device and Diagnostic Industry, 1999, XP002286594, pp. 96--, whole document.
Unknown author, Product information excerpt, Boehringer Ingelheim, from website http://www.torpex.com/product_information/, Aug. 11, 2003, pp. 1-4.
Unknown author, Product Information, Boerhinger Ingelheim, "Introducing TORPEX™ (aerosol albuterol sulfate): The Ultimate Tool for Equine Inhalation Treatment.", from website http://www.torpex.com/product_information/, Mar. 21, 2002, pp. 1-3.
Unknown author, Easivent valved holding chamber miscellaneous pictures, date unknown, pp. 1-5.
Unknown author, Pari LC Plus Instructions for Use (GB), Pari GmbH, dated Jul. 2001.
Unknown author, Pari LC Plus, LC Plus Turbo, LC Plus Junior, 2001, pp. 22-38.
Unknown author, Photographs of nebulizer manufactured by Pari GmbH with detached gas flow interrupter believed to have been publicly available prior to Feb. 13, 1996, 8 pages.
Unknown author, "Surface Resistivity" graph, origin and date unknown, 1 page.
Unknown author, "Pharmaceutical Aerosol Systems Division AeroSpacer* Collapsible Integrated Actuator with AeroCount Integra* Integrated Dose Indicator," Trudell Medical International, TMI—Aerosol Pharma Systems—AeroSpacer website, http://www.trudellrnedical.com/aerosol_aerospacer_callapsible.shtml, Mar. 7, 2003, p. 1 of 2.
Unknown author, "Asthma COPD Products Home Page," Trudell Medical International, TMI—Asthma COPD Products website , http://www.trudellmedical.com/copd_home.shtml, Mar. 7, 2003, p. 1 of 2.
Unknown author, "Preliminary Product Data, PermaStat® 1500-50D Polyester Thermoplastic Elastomer (TPE) Permanently Anti-Static ESD Protection 50-A Durometer," RTP Imagineering Plastics®, RTP Company Product Data Sheet website, http://www.rtpcompany.com/info/data/1500/PermaStat1500-50d.htm, Mar. 7, 2003, pp. 1-2.
Unknown author, "Preliminary Product Data PermaStat® 1200-70A Polyurethane Thermoplastic Elastomer (TPU) Permanently Anti-Static ESD Protection 70-A Durometer," RTP Company Product Sheet website, http://www.rtpcompany.com/info/data/1200/PermaStat1200-70A.htm, Mar. 7, 2003, pp. 1-2.
Unknown author, "Preliminary Product Data RTP 199 X 92520 Polypropylene (PP) Long Glass Fiber Flame Retardant," RTP Company Product Data Sheet Website, http://rtpcompany.com/info/data/0100/RTP199X92520.htm, Mar. 7, 2003, pp. 1-2.
Unknown author, "Preliminary Product Data PermaStat®100 Polypropylene (PP) Permanently Anti-Static ESD Protection," RTP Company Product Data Sheet website, http://www.rtpcompany.com/info/data/0100/PermaStat100.htm, Mar. 7, 2003, pp. 1-2.
Unknown author, "Preliminary Product Data PermaStat® 300 Polycarbonate (PC) Permanently Anti-Static ESD Protection," RTP Company Product Data Sheet website, http://www.rtpcompany.com/info/datapermastat/PermaStat300.htm, Mar. 7, 2003, pp. 1-2.
Unknown author, "Preliminary Product Data PermaStat® 600 Acrylonitrile Butadiene Styrene (ABS) Permanently Anti-Static ESD Protection," RTP Company Product Data Sheet website, http://rtpcompany.com/info/data/permastat/PermaStat600.htm, Mar. 7, 2003, pp. 1-2.
Unknown author, "Latest Innovations: Conductive Compounds, Typical conductive additives, "RTP Company—Typical conductive additives—Conductive Compounds website, http://www.rtpcompany.com/products/conductive/additives.htm, copyright 1995-2003 RTP Company, Mar. 7, 2003, pp. 1-3.
Unknown author, "Latest Innovations: Elastomer Compounds, "RTP Company—Thermoplastic Elastomer Compounds—Elastomer Compounds website, http://www.rtpcompany.com/products/elastomer/tpe.htm, copyright 1995-2003 RTP Company, Mar. 7, 2003, pp. 1-2.
Unknown author, "Latest Innovations: Conductive Compounds, PermaStat® Compounds," RTP Company—PermaStat® Compounds—Conductive Compounds website, http://www.rtpcompany.com/products/conductive/permastat/htm, copyright 1995-2001, Mar. 7, 2003, pp. 1-3.
Unknown author, "PermaStat® Compounds," RTP Company—PermaStat® Compounds (Conductive)—Data Sheets website,

(56) References Cited

OTHER PUBLICATIONS http://www.rtpcompany.com/info/data/permastat/index.htm, copyright 1995-2001, Mar. 7, 2003, pp. 1-4.
Unknown author, Pamphlet for "PARI PEP System", Part No. 18F61, published prior to Apr. 11, 2001, 3 pages.
Unknown author, Pamphlet for "TheraPEP:Positive Expiratory Pressure Therapy System", Catalog No. 20-1112, published prior to Apr. 11, 2001, 5 pages.
Unknown author, Photographs of Ventlab BreatheRite holding chamber, Dec. 2000, 3 pages.
Unknown author, Merriam-Webster's Collegiate Dictionary, Tenth Ed., p. 86, ISBN 0-87779-707-2, Sep. 1993, 2 pages.
Unknown author, "Technology Showcase Adjuncts to Bronchial Hygiene Therapy", AARC Times, May 1998, 2 pages.
Unknown author, Ventlab Corporation, "Ventlab BreatheRite," Web page from http://www.ventlab.com/mdi.htm, Dec. 15, 2000, 2 pages.
Unknown author, "AARC Clinical Practice Guideline: Use of Positive Airway Pressure Adjuncts to Bronchial Hygiene Therapy", Respiratory Care, May 1993, vol. 38 No. 5, pp. 516-520.
Unknown author, Respironics © OptiChamber Advantage chart, date unknown, 2 pages.
Wilson, R., "Positive Expiratory Pressure Therapy: the Key to Effective, Low-cost Removal of Bronchial Secretions", The Journal for Respiratory Care Practitioners, Mar. 1999, pp. 67-68.
Request for Inter Partes Reexamination of U.S. Pat. No. 7,562,656, issued Jul. 21, 2009, dated Aug. 3, 2009, 121 pages.
Corrected Request for Inter Partes Reexamination of U.S. Pat. No. 7,562,656 filed Oct. 26, 2009, 171 pages.
Notice of Allowability and Examiner-Initiated Interview Summary dated Aug. 6, 2009 for U.S. Appl. No. 11/452,100.
Application as filed for U.S. Appl. No. 09/287,997, filed Apr. 7, 1999, 65 pages.
Claims as filed for U.S. Appl. No. 08/938,686, filed Sep. 26, 1997, 8 pages.
Extended European Search Report for European Application No. 11172467.0, dated Dec. 5, 2011, 7 pages.
International Search Report for PCT/IB 01/00599 dated Nov. 9, 2001, 5 pages.
International Search Report in International Application No. PCT/IB03/01904, dated Oct. 1, 2003, 8 pages.
International Search Report for International Application No. PCT/IB2004/001132, dated Aug. 12, 2004, 5 pages.
Written Opinion of the International Search Authority for International Application No. PCT/IB2004/001132, dated Aug. 12, 2004, 7 pages.

\* cited by examiner

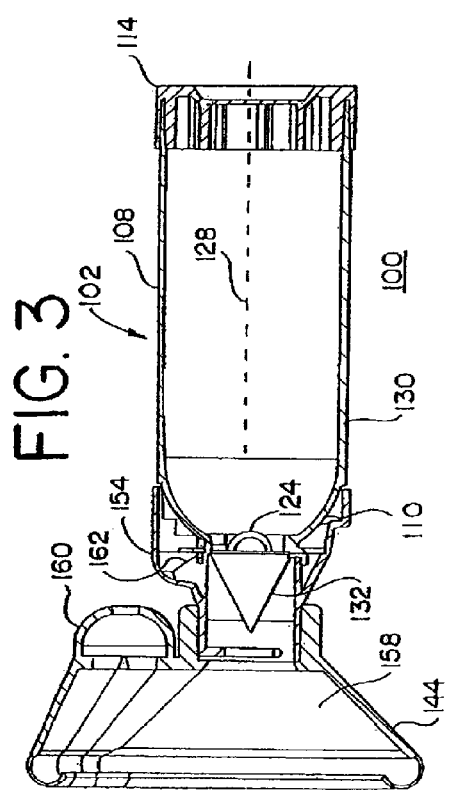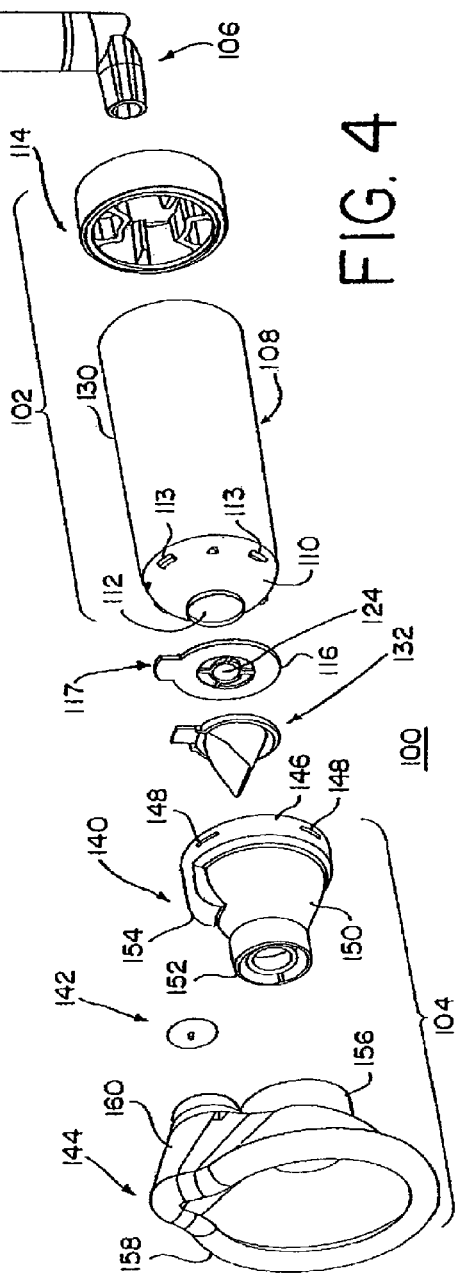

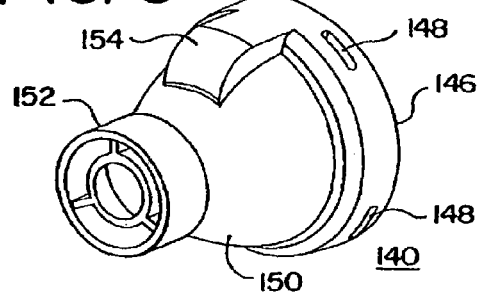
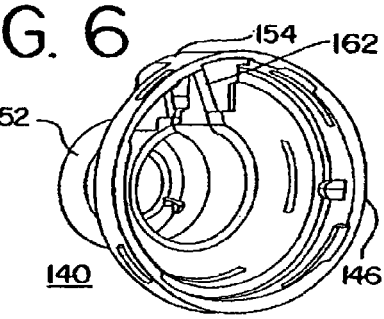
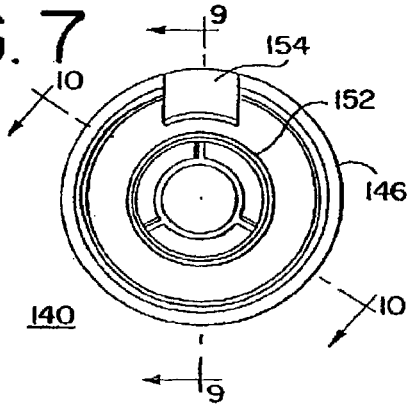
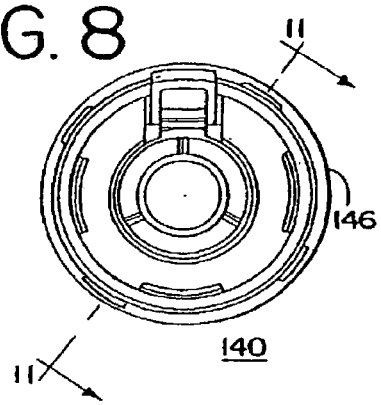
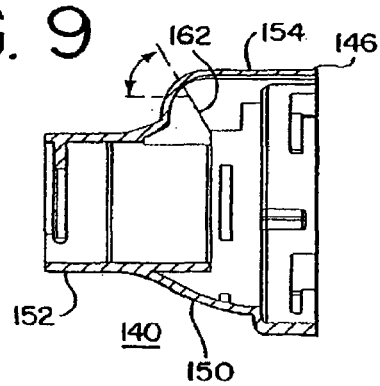
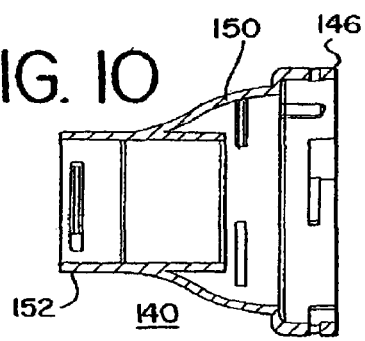
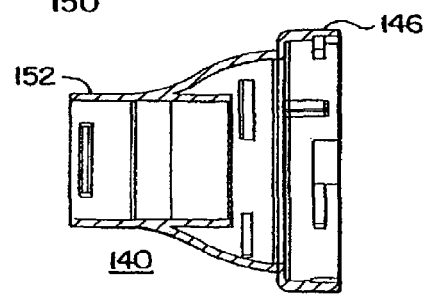

MEDICATION DELIVERY APPARATUS AND SYSTEM AND METHODS FOR THE USE AND ASSEMBLY THEREOF

This application is a continuation of U.S. patent application Ser. No. 13/313,876, filed Dec. 7, 2011, now U.S. Pat. No. 8,550,067, which is a continuation of U.S. patent application Ser. No. 11/712,547, filed Feb. 28, 2007, now U.S. Pat. No. 8,074,642, which is a continuation of U.S. patent application Ser. No. 11/130,808, filed May 17, 2005, now U.S. Pat. No. 7,201,165, which is a continuation of U.S. patent application Ser. No. 10/431,325, filed May 7, 2003, now U.S. Pat. No. 6,904,908, which claims the benefit of U.S. Provisional Patent Application 60/382,227, filed May 21, 2002, the entire disclosures of which are hereby incorporated herein by reference.

BACKGROUND OF THE INVENTION

Field of the Invention

The present invention relates to a visual indicator for an aerosol medication delivery apparatus and system used for administering a dosage of a substance in aerosol form to a patient.

Discussion of Related Art

The use of an aerosol medication delivery apparatus and system to administer medication in aerosol form to a patient's lungs by inhalation (hereinafter "aerosol delivery system(s)") is well known in the art. As used herein: the term "substance" includes, but is not limited to, any substance that has a therapeutic benefit, including, without limitation, any medication; the term "patient" includes humans and animals; and the term "aerosol delivery system(s)" includes pressurized metered-dose inhalers (pMDIs), pMDI add-on devices, such as holding chambers, devices including a chamber housing and integrated actuator suited for a pMDI canister, nebulizers and dry powder inhalers. Examples of such aerosol delivery systems are disclosed in U.S. Pat. Nos. 4,627,432, 5,582,162, 5,740,793, 5,816,240, 6,026,807, 6,039,042, 6,116,239, 6,293,279, 6,345,617, and 6,435,177, the entire contents of each of which are incorporated herein by reference. Conventional pMDIs typically have two components: 1) a canister component in which the medication particles and a propellant are stored under pressure in a suspension or solution form and 2) a receptacle component used to hold and actuate the canister and having a mouthpiece portion. The canister component typically includes a valved outlet from which the contents of the canister can be discharged. A substance is dispensed from the pMDI by applying a force on the canister component to push it into the receptacle component thereby opening the valved outlet and causing the medication particles to be conveyed from the valved outlet through the receptacle component and discharged from an outlet of the receptacle component. Upon discharge from the canister, the substance particles are "atomized" to form an aerosol.

In the case of pMDI holding chambers, the holding chambers typically include a chamber housing with a front end and a rear end. The mouthpiece portion of the pMDI receptacle is received in an elastomeric backpiece located at the rear end of the chamber housing. An example of such a backpiece is disclosed in U.S. Pat. No. 5,848,588, the entire contents of which are incorporated herein by reference. The front end of the chamber housing includes an inhalation valve or a containment baffle or both and an interface, such as an adapter, a mouthpiece and/or a mask. The interface can be coupled to the front end of the chamber housing or integrally molded to the front end of the chamber housing. Some holding chambers include an integrated receptacle for a pMDI canister thereby eliminating the need for a backpiece or other equivalent structure used to receive and hold the mouthpiece portion of a pMDI.

One problem that currently exists with many aerosol delivery systems is that there is a lack of a visual indication to alert a caregiver when a patient is inhaling. In the case of a pMDI used in conjunction with a holding chamber, for example, it is important for a caregiver to know if the patient is inhaling at a rate sufficient to open the inhalation valve to allow the aerosolized medication to exit the holding chamber. It is also important to know when the patient is inhaling in order to coordinate the actuation of the pMDI with inhalation.

The present invention proposes to overcome the above-described problem, and other problems as described further below, by using a visual indicator in an aerosol delivery system. Such a visual indicator is particularly helpful with patients who do not have established breathing patterns. These patients, such as infants and small children, generally have very low tidal volumes.

Some known holding chambers on the market maintain that it is possible to determine breathing patterns by looking through the chamber for the movement of the inhalation valve. This is difficult to do in the case of low tidal volumes when the valve will only move a minor amount. If the chamber has an accumulation of drug deposited on the walls then this further impedes the viewing. Several examples of such devices are discussed below. First, U.S. Pat. No. 5,385,140 discloses a holding chamber that has a crosscut valve with four petals that lift during inhalation. At lower tidal volumes the petals will lift a small amount, but this can be difficult to see since there are numerous supporting ribs directly in the line of sight. A second device is disclosed in U.S. Pat. No. 6,039,042 where a clear adapter is used to view breathing patterns by way of the valve. However, the inhalation portion of the valve that moves is directly in the drug pathway and has only slight movement at lower flow rates (approximately 20°). Note that the entire contents of U.S. Pat. Nos. 5,385,140 and 6,039,042 are incorporated herein by reference.

With some of the other devices on the market it is possible to view the exhalation portion of the breath, but this is not considered to be as important as seeing the inhalation portion. One such device is disclosed in U.S. Pat. No. 6,293,279, the entire contents of which are incorporated herein by reference. The device has a mask with an exhalation valve that moves during exhalation, but at the lower tidal volumes this movement is not obvious.

Another problem that occasionally occurs, when the interface includes a mask, is a poor seal between the patient's face and the mask. Such a poor seal may adversely affect the delivery of aerosolized medication to the patient. The use of the above-mentioned visual indicator would be helpful in alerting the caregiver to verify whether there is a poor seal between the patient's face and the mask and, if so, to readjust the mask on the patient's face to improve the seal.

SUMMARY OF THE INVENTION

One aspect of the present invention regards a delivery system that includes a chamber that contains a substance in an interior volume of space formed within said chamber and an opening that receives the substance located in said volume of space and introduces the substance to a downstream path upon which the substance primarily flows along.

An interface that receives the substance from the opening, the interface has a viewing port that prevents substantially non-ambient atmosphere gases and substances from escaping therefrom and that allows visualization of an internal portion of the interface. A flow indicator is positioned within the interface so as to be viewed via the viewing port and is positioned so as to not substantially interfere with a flow of the substance along the path.

A second aspect of the present invention regards a method of determining whether a patient is inhaling or exhaling when using a delivery system, the method including dispensing a substance located within an interior volume of a delivery system so that the substance will primarily flow along a path within the delivery system after being dispensed. Observing a position of a flow indicator located within the delivery system and located so as not to substantially interfere with the substance flowing along the path. Determining whether a user of the delivery system is inhaling from the delivery system based on the observed position of the flow indicator.

A third aspect of the present invention regards a flow indicating system that includes a conduit that contains a substance, wherein the conduit defines a path along which the substance primarily flows and a viewing port attached to the conduit and the viewing port that prevents substantially non-ambient atmosphere gases and substances from escaping therefrom and allows visualization of an internal space defined by the viewing port. A flow indicator that is positioned within the conduit so as to be viewed via the viewing port and is positioned so as to not substantially interfere with a flow of the substance along the path.

Each aspect of the present invention provides the advantage of assisting either the patient or a third party caregiver to determine when the patient is inhaling when using an aerosol delivery system so that the patient or third party caregiver can be alerted to possible causes affecting inhalation, such as an improper seal between the patient's face and the aerosol delivery system's interface, such as a mask.

Each aspect of the present invention provides the advantage of allowing a user or caregiver to observe when inhalation has begun so that the drug can be properly administered.

The foregoing and other features and advantages of the invention will become further apparent from the following detailed description of the presently preferred embodiments, read in conjunction with the accompanying drawings.

BRIEF DESCRIPTION OF SEVERAL VIEWS OF THE DRAWINGS

FIG. 3 is a side cross-sectional view of the aerosol delivery system of FIG. 1;

FIG. 4 is a perspective exploded view of the aerosol delivery system of FIG. 1;

FIG. 5 is a front perspective view of an embodiment of an adapter according to the present invention to be used with the aerosol delivery system of FIG. 1;

FIG. 6 is a rear perspective view of the adapter of FIG. 5;

FIG. 7 is a front view of the adapter of FIG. 5;

FIG. 8 is a rear view of the adapter of FIG. 5;

FIG. 9 is a cross-sectional view of the adapter of FIG. 5 taken along line 9-9 of FIG. 7;

FIG. 10 is a cross-sectional view of the adapter of FIG. 5 taken along line 10-10 of FIG. 7;

FIG. 11 is a cross-sectional view of the adapter of FIG. 5 taken along line 11-11 of FIG. 8;

DETAILED DESCRIPTION OF THE PREFERRED EMBODIMENTS

Figure 1:
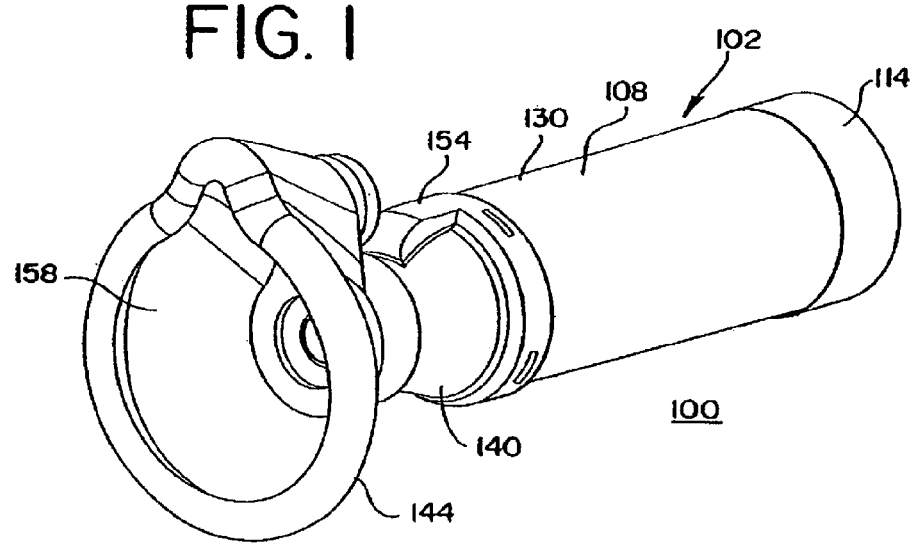
FIG. 1 is a perspective view of an embodiment of an aerosol delivery system in accordance with the present invention.
Figure 2:
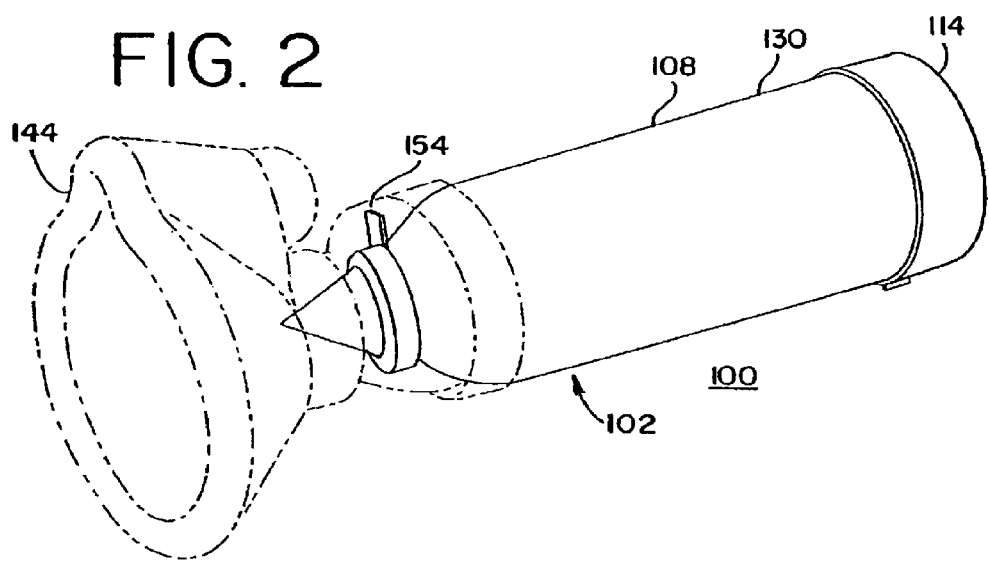
FIG. 2 is a perspective and partially transparent view of the aerosol delivery system of FIG. 1.
Figure 12:
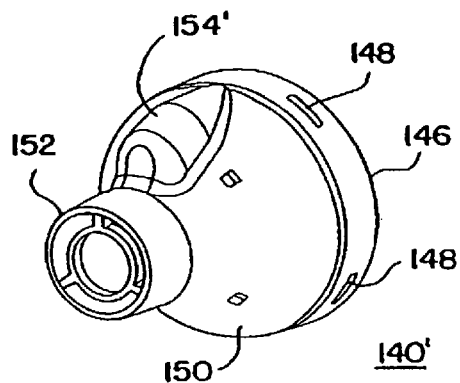
FIG. 12 is a front perspective view of a second embodiment of an adapter according to the present invention to be used with the aerosol delivery system of FIG. 1.
Figure 13:
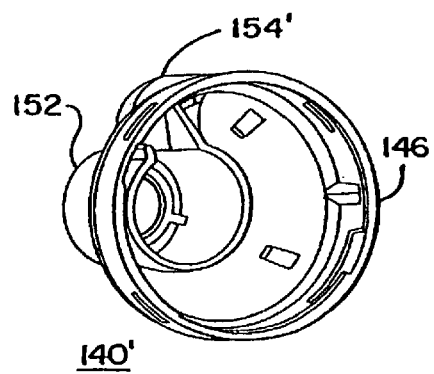
FIG. 13 is a rear perspective view of the adapter of FIG. 12.
Figure 14:
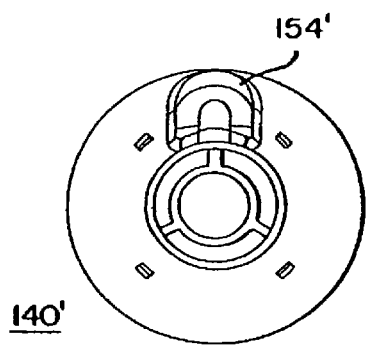
FIG. 14 is a front view of the adapter of FIG. 12.
Figure 15:
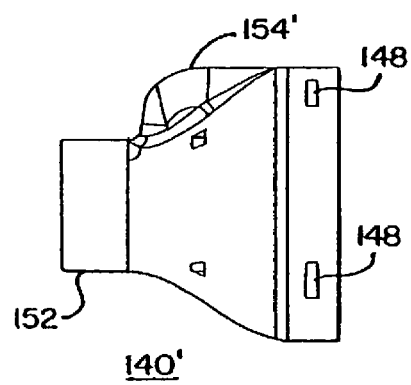
FIG. 15 is a side view of the adapter of FIG. 12.
Figure 16:
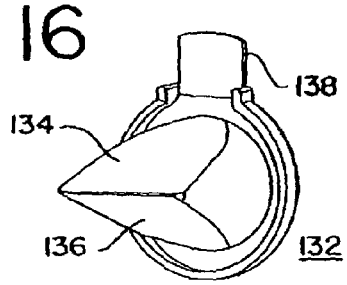
FIG. 16 is a front perspective view of an embodiment of a valve according to the present invention to be used with the aerosol delivery apparatus of FIG. 1.
Figure 17:
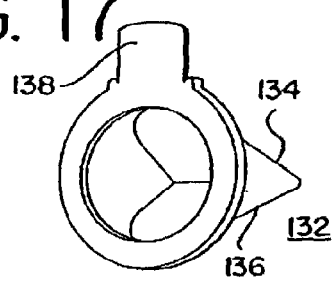
FIG. 17 is a rear perspective view of the valve of FIG. 16.
Figure 18:
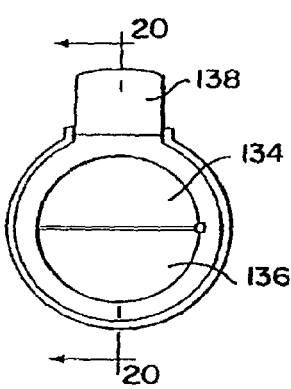
FIG. 18 is a front view of the valve of FIG. 16.
Figure 19:
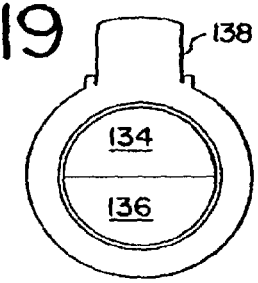
FIG. 19 is a rear view of the valve of FIG. 16.
Figure 20:
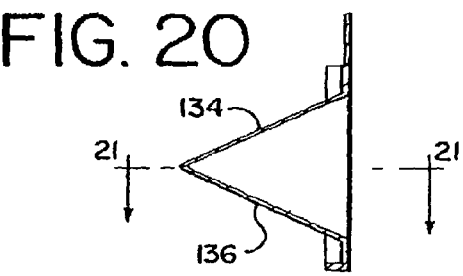
FIG. 20 is a cross-sectional view of the valve of FIG. 16 taken along line 20-20 of FIG. 18.
Figure 21:
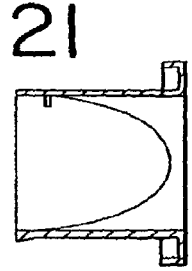
FIG. 21 is a cross-sectional view of the valve of FIG. 16 taken along line 21-21 of FIG. 20.

FIGS. 1-11, 16-21 and 25-29 show an embodiment of an aerosol delivery system 100. The system 100 includes a holding chamber or conduit 102, an interface 104, a retaining disc 116, an inhalation valve 132 and a source of a substance, such as a pMDI canister 106, attached to the rear end of the holding chamber 102.

As shown in FIGS. 1-4 and 27-34, the holding chamber 102 includes a chamber housing 108 that has a generally cylindrical cross-sectional shape that defines an interior volume of space for receipt therein of aerosolized medication from the pMDI 106. A front end of the chamber housing 108 includes a dome-shaped head piece 110 that includes a central circular opening 112 that is in fluid communication with the interior volume of space of the chamber housing 108. The opening 112 defines the periphery of a flow path as it exits the opening. The head piece 110 further includes a plurality of engagement tabs 113, whose function will be described below. A rear end of the chamber housing 108 is attached to a detachable and flexible backpiece 114 that includes an opening (not shown) suited to receive the mouthpiece portion of the pMDI receptacle that houses the pMDI canister. The backpiece 114 preferably is substantially the same as the backpiece disclosed in U.S. Pat. No. 5,848,588. Examples of possible pMDI adapters and canisters to be used in conjunction with the holding chamber 102 are also described in U.S. Pat. Nos. 5,012,803, 5,012,804, 5,848,588 and 6,293,279, the entire contents of each of which is incorporated herein by reference.

When a force is applied to the stem of the pMDI canister a portion of the substance is discharged from the discharge end of the pMDI receptacle in aerosol form into the chamber housing 108. The aerosol medication particles within the chamber housing 108 are withdrawn therefrom by having the patient inhale through the interface 104 in the manner described below.

The pMDI canister contains a substance, preferably a medication suspension or solution under pressure. In the present embodiment, the substance dispensed is an HFA propelled medication suspension or solution formulation. Other propellants, such as CFC may also be used. It should be pointed out that while the described embodiments regard an aerosol delivery system for the delivery of an aerosolized medication from a pMDI, other aerosol delivery systems are contemplated that can be used within the spirit of the present invention. For example, it is contemplated that a visual indicator can be incorporated with an aerosol delivery system such as existing ventilator systems, dry powder inhalers and nebulizers, in a manner similar to that described below. Examples of nebulizers that can be adapted to include a visual indicator are disclosed in U.S. Pat. Nos. 5,823,179 and 6,044,841, the entire contents of which are incorporated herein by reference.

The present invention is not limited to the treatment of human patients. For example, it is contemplated that a visual indicator can be incorporated in a mask for administering medication to animals, including for example and without limitation equines, cats, dogs, etc. An example of an equine mask is disclosed in U.S. Pat. No. 5,954,049, the entire contents of which are incorporated herein by reference. With such aerosol delivery systems in mind, the variety of medications that can be dispensed by aerosol delivery systems that employ a visual indicator in accordance with the present invention is increased.

Figure 25:
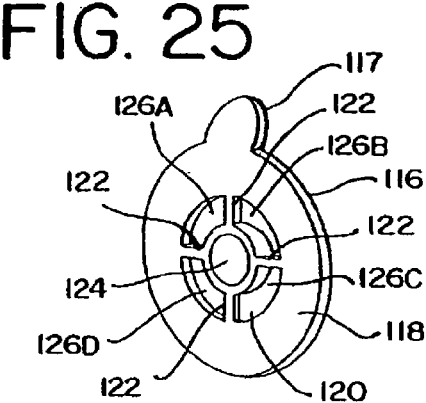
FIG. 25 is a perspective view of an embodiment of a retaining disc according to the present invention to be used with the aerosol delivery system of FIG. 1.
Figure 26:
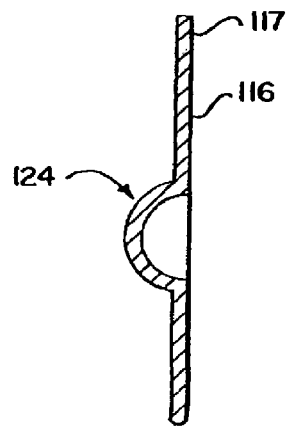
FIG. 26 is a side-view of the retaining disc of FIG. 25.
Figure 27:
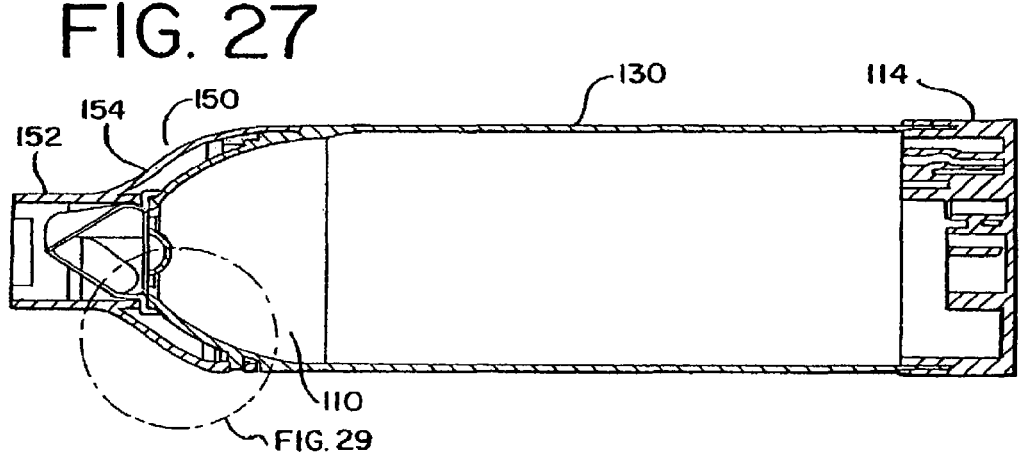
FIG. 27 is a side cross-sectional view of an embodiment of an aerosol delivery system according to the present invention taken along line 27-27 of FIG. 28 that can be used with the aerosol delivery system of FIG. 1.
Figure 28:
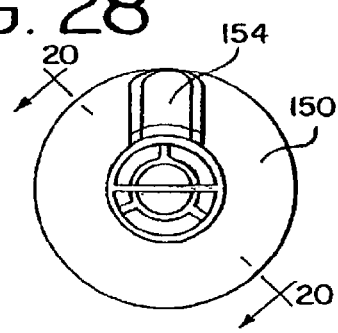
FIG. 28 is a front view of the aerosol delivery system of FIG. 27.
Figure 29:
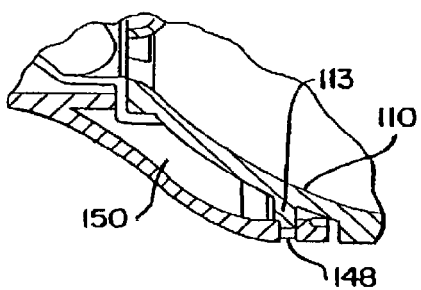
FIG. 29 is an enlarged portion of the circled area of the aerosol delivery system of FIG. 27.

As shown in FIG. 4, a retaining disc 116 is positioned before the opening 112 at the front end of the chamber housing 108. The retaining disc 116 may be integrally attached to the chamber housing 108 or releasably attached as shown in FIG. 4. As shown in FIGS. 4 and 25-26, the retaining disc 116 includes an annular ring 118 that surrounds an opening 120. Four linear appendages 122 extend inwardly from the annular ring 118 and are attached to a circular dome portion 124. The annular ring 118, the appendages 122 and the dome portion 124 define an inhalation opening area 126 that includes four openings 126A-126D. The openings 126A-D are arcuate in shape. The openings have an inner radius of approximately 10 mm and an outer radius of approximately 18 mm. Each opening has an arcuate length of 4 mm. The size, shape and number of openings may vary depending on the medication and/or propellant used. The retaining disc 116 is preferably made of a rigid material, such as a metal or plastic, preferably propylene or polycarbonate. As shown in FIGS. 4, 25 and 26, the retaining disc 116 includes a semi-circular stop 117 whose operation will be explained below. Other examples of possible retaining discs are disclosed in U.S. Pat. No. 6,293,279, the entire contents of which are incorporated herein by reference. The annular ring 118 is attached to the front end of the chamber housing 108 so that the openings 112 and 120 are concentric and overlap one another.

The center portion of the retaining disc 116 includes a containment baffle positioned so as to partially block the opening 112. The retaining disc 116 reduces the velocity or flow rate or both of the aerosol medication particles flowing along the axis 128 of the chamber housing 108. The circular dome portion 124 of the retaining disc 116 is aligned with the central axis 128 of the chamber housing 108 and is directly in line with the opening 112. Aerosol medication particles that have a flow path away from the central axis 128 tend to have a velocity that is lower than that of particles near to the axis 128. The dome portion 124 of the retaining disc 116 reduces the forward, on-axis velocity and simultaneously acts as an impaction surface for on-axis projectile aerosol medication particles and so protects the duckbill valve 132. At the same time, the dome portion 124 allows slower moving aerosol medication particles to migrate towards the sides 130 of the chamber housing 108. The forward velocity of the aerosol medication particles away from the axis 128 along the chamber length is also reduced by the annular ring 118 of the retaining disc 116. It should be understood that the dome portion can alternatively be formed with a flat surface facing the rear end, or a curved surface, for example a convex or concave surface.

As shown in FIG. 4, a duckbill valve 132 is seated on the front surface of the annular ring 118. The duckbill valve 132 is generally well known in structure having a top surface 134 and a bottom surface 136. The surfaces 134 and 136 open and close with respect to each other in a well-known manner so as to allow or prevent gas to flow through the valve 132. The duckbill valve 132 preferably is a 19 mm valve made of a soft plastic, such as silicone or a thermoplastic elastomer. It should be understood that other valves, including for example and without limitation, center post valves, slit petal valves and valves having a central opening with a peripheral sealing edge.

Figure 22:
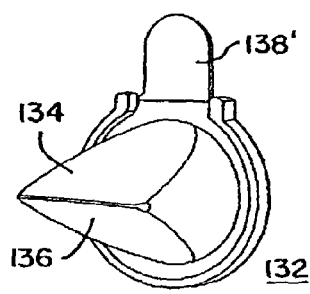
FIG. 22 is a front perspective view of a second embodiment of a valve according to the present invention to be used with the aerosol delivery apparatus of FIG. 1.
Figure 23:
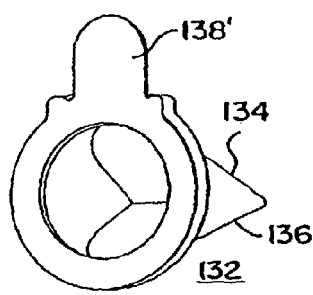
FIG. 23 is a rear perspective view of the valve of FIG. 22.
Figure 24:
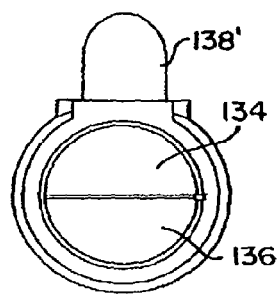
FIG. 24 is a front view of the valve of FIG. 22.

On the top portion of the duckbill valve 132, a visual flow indicator 138 is integrally attached to a top portion of the outer circumference of the duckbill valve 132. The visual flow indicator 138 is rectangular in shape, although other shapes, such as a square or an ellipse, may also be suitable. For example, the visual flow indicator 138' may have a rounded top edge as shown in FIGS. 22-24. The rectangular and rounded visual flow indicators 138, 138' each may have a length of 5 mm to 20 mm, preferably a length between 7 mm and 11 mm, and most preferably a length of 8.5 mm, a width of 5 mm-20 mm, preferably 8 mm to 12 mm, and most preferably 10 mm, and a thickness of 0.1 to 2 mm, preferably 0.15-1 mm, and most preferably 0.25 mm. The length of the visual flow indicators 138, 138' are measured from a hinge area (not shown). With this in mind, the sensitivity of the visual flow indicators 138, 138' is a function of the length of the indicator, wherein the indicator becomes longer it becomes more sensitive to detecting flow. The operation of the visual flow indicators 138, 138' will be described in more detail below.

The flow indicator can be integrally formed with the valve or it can be made as a separate member. The indicator 138, 138' is hingedly connected to the valve with a living hinge formed at the junction thereof, or it can be hingedly connected with a pin. The resiliency of the indictor 138, 138' biases the indicator to an at rest position. However, it should be understood that auxiliary springs can be configured to act on the indicator to bias it to the at rest position.

As described above, the chamber housing 108, retaining disc 116 and duckbill valve 132 define a holding chamber 102. The holding chamber 102 is attached to a patient interface 104, although a patient interface integrally molded with the front end of the chamber housing 108 would also be suitable. In one embodiment, the patient interface 104 includes an adapter 140 and a mask 144 with exhalation valve 142. Other patient interfaces may include for example and without limitation, various mouthpieces, masks, endotracheal tubes, etc. As shown in FIGS. 4-11, the adapter 140 includes an annular attachment collar 146 with slots 148, a transition piece 150 and a cylindrical exit port 152. The adapter 140 is attached to the chamber 108 by snap inserting the tabs 113 of the chamber housing 108 into the slots 148 and then twisting the chamber housing 108 or adapter 140 so that the tabs 113 are locked into place within the slots 148. Once the chamber housing 108 is attached to the adapter 140, the duckbill valve 132 and the flow indicator 138, 138' are positioned within the transition piece 150. In particular, the flow indicator 138, 138' is positioned within a raised viewing port area 154 of the transition piece 150. Since the adapter 140 with its transition piece 150 and raised viewing port area 154 are each made of a clear rigid plastic, such as polycarbonate or a co-polyester, the movement of the flow indicator 138, 138' is visible to a user at all times. In another variation, the viewing port area 154 is formed in the collar 146 and the indicator 138, 138' is positioned therein.

Figure 43:
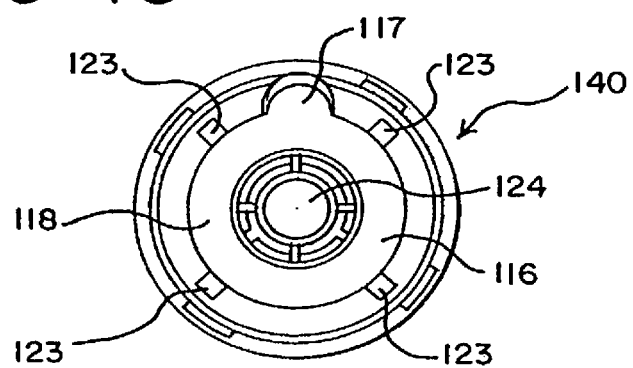
FIG. 43 shows a rear view of an alternative embodiment of an adapter.
Figure 44:
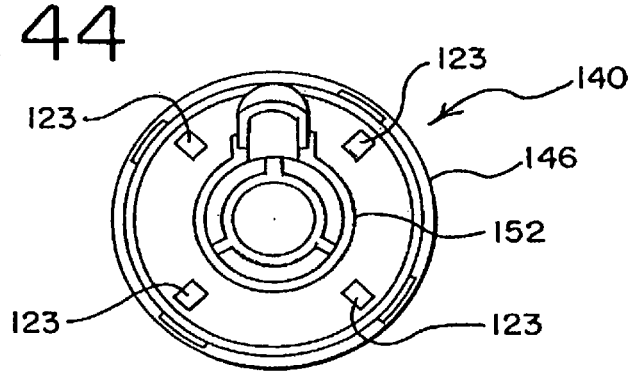
FIG. 44 shows a retainer releasably connected to the adapter shown in FIG. 43.

As explained above, the retaining disc 116 is positioned at the front end of the chamber housing, and can be integrally attached thereto or releasably detached, for example by disposing it between the chamber housing and the adapter 140. In one embodiment, shown in FIGS. 43 and 44, the retaining disc 116 is releasably connected to the adapter 140, or other patient interface component. In one embodiment, a plurality of tabs 123 are formed on the interior of the adapter and engage the outer peripheral edge of the annular ring 118 in a snap-fit engagement. In other embodiments, the retaining disc is integrally molded with the adapter or other patient interface component, or is secured thereto by bonding, fasteners and other similar devices. In this way, the retaining disc 116, and the valve 132 that is seated thereon between the adapter and the retaining disc, remain coupled to the adapter 140, or other similar component secured to the end of the chamber housing, upon its removal, for example when cleaning the device. Accordingly, the risk of losing the retaining disc 116 and/or valve 132 is reduced.

Note that an alternate embodiment of an adapter is shown in FIGS. 12-15. The adapter 140' has similar dimensions and elements as the adapter of FIGS. 5-11. Operation and attachment are similar as well. One difference is the shape of the viewing port area 154' in which the indicator 138, 138' is positioned.

An exhalation valve 142 is inserted into an exit port formed in the nasal reception area 160 of the mask 144 and attached thereto. Examples of such a mask and exhalation valve are disclosed in U.S. Pat. Nos. 5,988,160 and 5,645,049, the entire contents of each of which are incorporated herein by reference. A cylindrical input port 156 of the mask 144 is placed over the exit port 152 of the adapter 140, 140' and attached thereto by a friction fit.

With the above description of the structure of the aerosol delivery system 100, the operation of the system 100 can be readily understood. In particular, a patient places his or her face within the interior 158 of the mask 144 so that his or her nose is positioned within the nasal reception area 160. In other embodiments, the patient or caretaker arranges the patient interface, such as a mouthpiece or endotracheal tube in appropriate registration with the user. The patient or caretaker then presses the pMDI canister within the pMDI adapter of the pMDI 106 attached to the backpiece 114 located at the rear end of the chamber housing 108, which causes the medication to be delivered in aerosol form to the opening 112 in the manner described previously.

Figure 33:
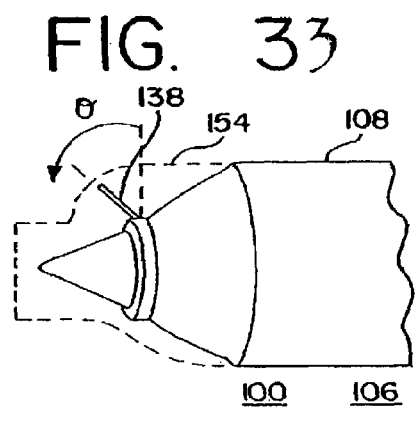
FIG. 33 is a side and partially transparent view of a portion of the aerosol medication delivery system of FIG. 1 showing a flow indicator at an inhalation position.
Figure 34:
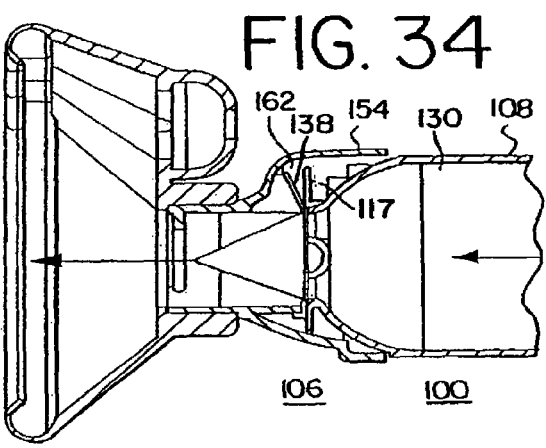
FIG. 34 is a side-cross sectional view of the aerosol delivery system of FIG. 1 showing a flow indicator at an inhalation position.

At or just after the time of depressing the pMDI canister, the patient inhales. During proper inhalation, the visual flow indicator 138 will pivot forward in response to the inhalation pressure by an angle θ of between 25° to 45°, and preferably 45°, and seal against a surface 162 on the adapter 140, 140' as shown in FIGS. 3 and 33-34. The angle θ can be varied to take into account the attributes of the patient, i.e., child v. infant. Note that the visual flow indicator 138 has minimal resistance, due to its size and shape, and will respond to low tidal volumes, which is ideal for infants (tidal volume of approximately 50 cc, flow rate approximately 5 lpm) and small children (tidal volume ranging from approximately 150 to 250 cc, flow rate approximately 12 lpm). The movement of the visual flow indicator 138, 138' against surface 162 creates a seal that will prevent entrainment of ambient air. A caregiver who directs his or her attention to the viewing port area 154, 154' will be able to see the movement of the flow indicator 138, 138' as it forms the seal and so will become aware that inhalation is occurring or has occurred. Also during inhalation, the duckbill valve 132 will open thereby allowing the aerosolized medication to exit the chamber housing 108 and be introduced by the opening 112 to a downstream path upon which the medication flows along so as to eventually be inhaled by the patient. As shown in FIGS. 2 and 31-34, the flow indicator 138, 138' is positioned above the duckbill valve 132 and outside the periphery of opening 112, and so is outside of the medication dispensing pathway, and thus does not compromise medication delivery. Note that the introduction of the medication to the pathway through the opening 112 can be caused by either external or internal forces.

Figure 31:
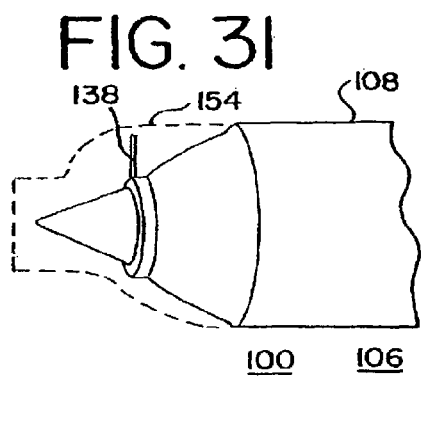
FIG. 31 is a side and partially transparent view of a portion of the aerosol delivery system of FIG. 1 showing a flow indicator at a rest position.
Figure 32:
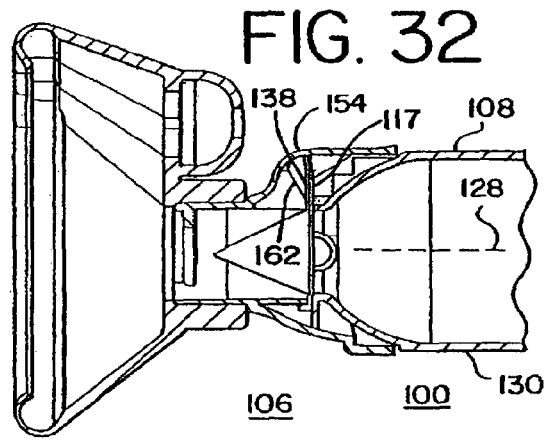
FIG. 32 is a side-cross sectional view of the aerosol medication delivery system of FIG. 1 showing a flow indicator at a rest position.

Once the patient exhales or ceases to inhale, the flow indicator 138, 138' will pivot back to its original vertical position until it engages the stop 117 as shown in FIGS. 31-32. The resiliency of the indicator 138, 138' pivots or biases the indicator to the at-rest position. Again, a caregiver who directs his or her attention to the viewing port area 154, 154' will be able to see the return movement of the flow indicator 138, 138' and so will become aware that exhalation has occurred. Besides alerting the caregiver that inhalation or exhalation is occurring or has occurred, the movement of the flow indicator gives the caregiver confidence that, where the patient interface includes a mask, a proper seal is formed between the patient's face and the mask 144.

Note that the flow indicator 138, 138' does provide a pathway which is in fluid contact with ambient air located within the viewing port area 154, 154' rearward of the flow indicator 138, 138'. The pathway includes a rearward opening or an opening formed in the rearward top portion of the viewing port area 154, 154', such that the flow indicator 138, 138' is drawn off of the stop. However, the flow indicator 138, 138' seals against surface 162 to prevent the entrainment of ambient air as described above.

Figure 30:
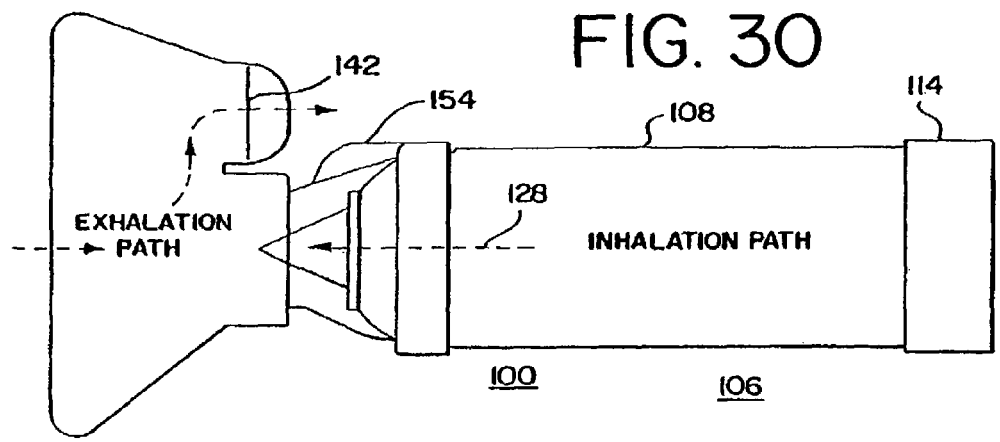
FIG. 30 is a side and partially transparent view of the aerosol delivery system of FIG. 1 showing exhalation and inhalation paths.

The primary pathway for exhaled gases is through the exhalation valve 142 located in the mask 144 as shown in FIG. 30. In particular, the stop 117 and flow indicator 138, 138' extend so as to substantially block all exhaled gases from escaping via the viewing port while allowing ambient air to flow therein. Similarly, the stop 117 and flow indicator 138, 138', which is registered against surface 162 upon inhalation, substantially blocks the dispensed substance from exiting the delivery system via the viewing port area. Accordingly, the stop 117 and flow indicator 138, 138' substantially prevents non-ambient gases and substances from escaping from the delivery system via the viewing port area. Note that the stop 117 may be removed so as to allow the viewing port area to act as a two-way valve that allows ambient atmosphere to enter and exhalation gases to exit therefrom.

Figure 35:
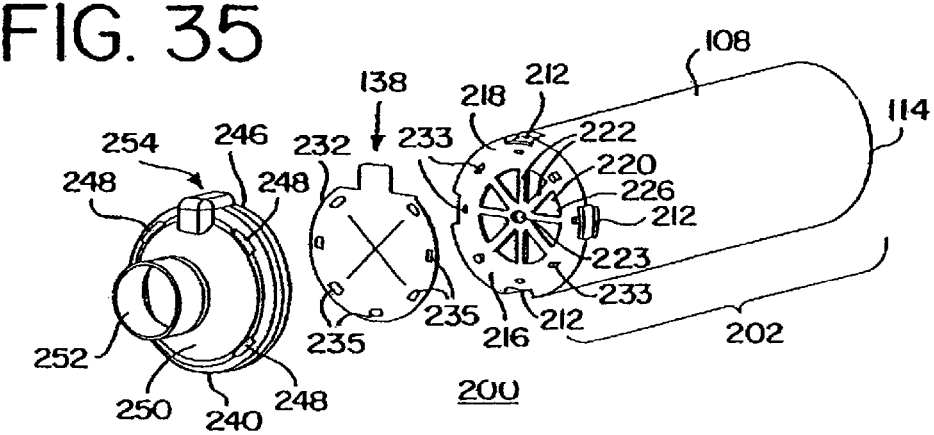
FIG. 35 shows a perspective and exploded view of a second embodiment of an aerosol delivery system according to the present invention.

An alternative embodiment of an aerosol delivery system is shown in FIG. 35. The aerosol delivery system 200 is the same as the aerosol delivery system 100 of FIGS. 1-11, 16-21 and 25-29 except that the holding chamber and the patient interface have been altered as shown in the drawings and as described herein. Accordingly, like elements will retain like numerals. With this in mind, the holding chamber or conduit 202 has a backpiece 114 attached to a rear end of the chamber housing 108. An opening of the backpiece 114 receives a discharge end of an adapter (not shown) that houses the pMDI canister. The holding chamber 202 further includes a retaining disc 216 that is integrally attached to a front end of the cylindrical chamber housing 108. The retaining disc 216 includes an annular ring 218 that surrounds an opening 220. Eight linear appendages 222 extend inwardly from the annular ring 218 and meet at a center hub 223. The annular ring 218, the appendages 222 and the center hub 223 define an inhalation opening area 226 that includes eight openings. The size, shape and number of the openings may vary depending on the medication and/or propellant used.

As shown in FIG. 35, a petal valve 232 is attached to the front surface of the annular ring 218. In particular, pegs 233 integrally formed on the annular ring 218 are snugly inserted into corresponding openings 235 formed in the petal valve 232. The operation of the petal valve 232 is well known in the art. The petal valve is preferably made of a material similar to that of the duckbill valve 132. On the top portion of the petal valve 232, a visual flow indicator 138, 138' is integrally attached to a top portion of the outer circumference of the petal valve 232.

The holding chamber or conduit 202 is attached to an interface similar to the interface 104 shown in FIGS. 1-11, 16-21 and 25-29. The interface of the embodiment of FIG. 35 differs from the interface 104 in that a shorter adapter 240 is used, which includes a cylindrical exit port 252 that can function as a mouthpiece. Alternatively, the adapter 240 can be attached to an exhalation valve and a mask (not shown) in the manner described with respect to FIGS. 1-11, 16-21 and 25-29. As shown in FIG. 35, the adapter 240 includes an annular attachment collar 246 with slots 248, a transition piece 250 and a cylindrical exit port 252. The adapter 240 is attached to the chamber housing 108 by snap inserting tabs 212 of the chamber housing 108 into the slots 248 and then twisting the chamber housing 108 or adapter 240 so that the tabs 212 are locked into place within the slots 248. Once the chamber housing 108 is attached to the adapter 240, the petal valve 232 and the flow indicator 138, 138' are positioned within the transition piece 250. In particular, the flow indicator 138, 138' is positioned within a raised viewing port area 254 of the transition piece 250. The adapter 240 with its transition piece 250 and raised viewing port area 254 are each made of a clear rigid plastic, such as polycarbonate or a co-polyester. The chamber housing 108 can also be made of a clear material, such as a rigid plastic. Thus, a caregiver is able to visualize the movement of the visual flow indicator 138, 138' within the adaptor 240 and is able to detect whether inhalation is being performed or a proper seal is present in the same manner as with the aerosol delivery system of FIGS. 1-11, 16-21 and 25-29. The adapter can also include a stop member that interfaces with the flow indicator.

In each of the embodiments shown in FIGS. 1-35, the visual flow indicator 138, 138' is integrally attached to its corresponding valve. It should be pointed out that such integral attachment is not necessary. For example, it is possible to take a separate piece of material in the shape and composition of indicator 138, 138' and attach one end to a portion of the adapter so that a free end of the material lies within the viewing port. Attachment can be accomplished by inserting the one end between two ridges formed in the adapter and gluing the end therebetween.

Figure 36:
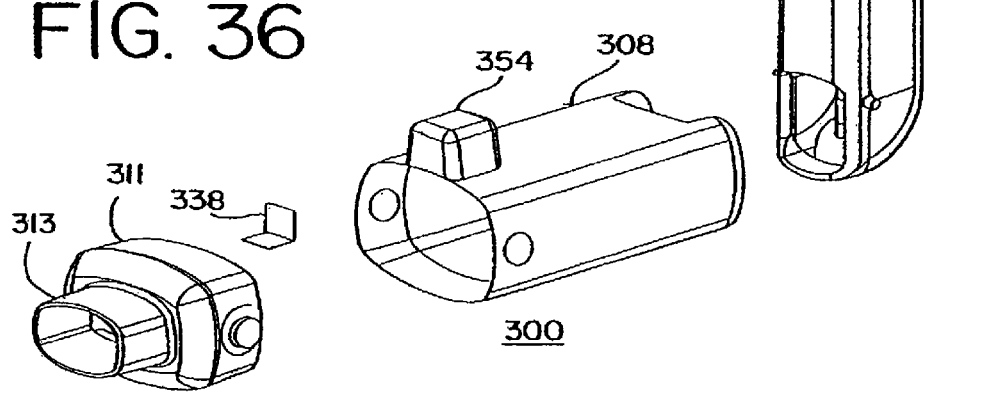
FIG. 36 shows a perspective and exploded view of a third embodiment of an aerosol delivery system according to the present invention.

Another example of where the visual flow indicator is not attached to a valve is shown in FIG. 36. In this embodiment, a visual flow indicator 338 is attached to an aerosol delivery system 300 similar to the one disclosed in U.S. Pat. No. 6,293,279. One difference is that the chamber housing 308, attached to the canister holding portion 309, includes a transparent viewing port 354. In an alternative embodiment, the view port can be formed on the downstream portion 311 of the delivery system. The visual flow indicator 338 is attached to either the chamber housing 308 or the downstream portion 311 that includes the mouthpiece 313 via a snap fit. The visual flow indicator 338 preferably has a shape and a structure similar to that of the visual flow indicators 138, 138' described previously so as to have a similar range of motion. In operation, the chamber housing 308 acts as a conduit of the substance as it travels to the mouthpiece 313.

Figure 37:
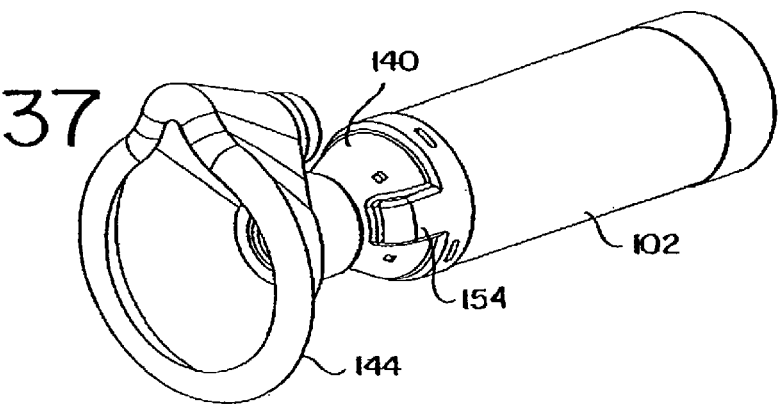
FIG. 37 shows a perspective view of a fourth embodiment of an aerosol delivery system according to the present invention.

Other variations for the visual flow indicator are also possible. For example, the viewing port area can be positioned elsewhere on the adapters 140, 240, the chamber housing 308 and the downstream portion 311 and the corresponding visual flow indicator is positioned so as to be viewed from the viewing port area. In the case of the aerosol delivery system of FIGS. 1-11, 16-21 and 25-29, the viewing port area can be moved to the side of the adapter 140 in the manner shown in FIG. 37. In such a case, the corresponding visual flow indicator 138, 138' is moved to a side of the duckbill valve 132 that faces the viewing port area 154, 154'.

Figure 38:
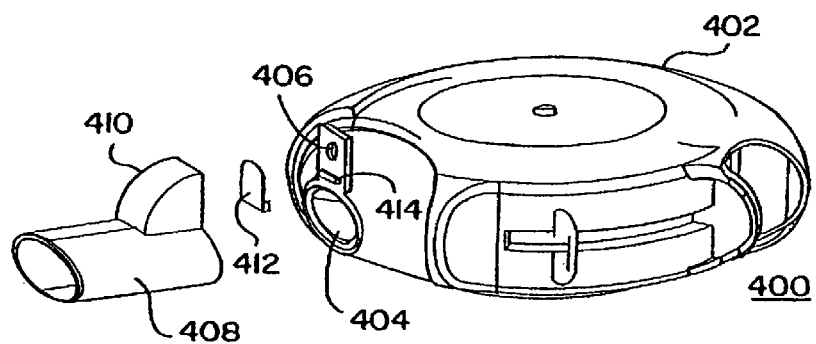
FIG. 38 shows a perspective, exploded view of an embodiment of a dry powder inhaler delivery system according to the present invention.
Figure 39:
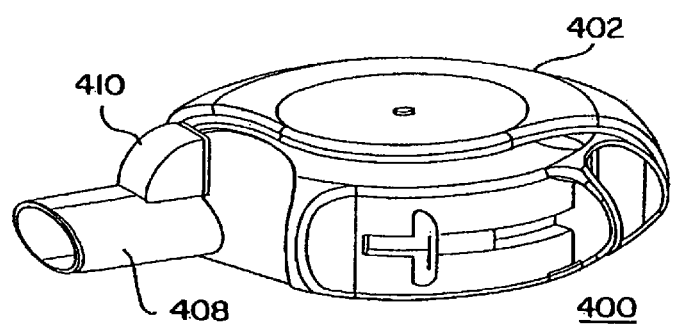
FIG. 39 shows a perspective view of the dry powder inhaler delivery system of FIG. 38.

FIGS. 38-42 show the present invention used in aerosol delivery systems such as dry powder inhalers and nebulizer systems. In the case of dry powder inhalers, a dry powder inhaler 400 includes a chamber housing 402 that contains a dry powder as shown in FIGS. 38 and 39. The chamber housing 402 is similar to the chamber housing disclosed in U.S. Pat. No. 4,627,432, the entire content of which is incorporated herein by reference. Other dry powder inhalers that can incorporate a flow indicator are disclosed for example and without limitation in U.S. Pat. No. 6,116,239, which is hereby incorporated herein by reference. The chamber housing 402 includes a circular bottom opening 404 and a top opening 406 that is in fluid communication with ambient air. An interface which includes a conduit or mouthpiece 408, is attached to the bottom opening 404 so that the mouthpiece 408 is in fluid communication with the interior of the chamber housing 402. Attached to the mouthpiece 408 is a transparent viewing port area 410. Within the viewing port area 410, a visual flow indicator 412 is positioned. The visual flow indicator 412 has a rear, lower slot (not shown) that receives a ridge 414 formed below the top opening 406. Once the ridge 414 is received in the rear slot, the visual flow indicator 412 is permanently attached to the ridge 414 by using an adhesive.

In operation, the patient activates the chamber housing 402 to provide access to the dry powder within by having the patient inhale through the mouthpiece 408. Upon inhalation, the dry powder substance within the housing 402 is introduced by the opening 404 to a downstream path along which the substance travels through the interface and the mouthpiece 408 to reach the patient. During inhalation the upper part of the visual flow indicator 412 will pivot downward to a horizontal position. If the patient is not inhaling or fails to inhale above a specified rate of inhalation, the upper part of the visual flow indicator 412 will remain in a vertical position blocking top opening 406. The range of motion of the visual flow indicator 412 is preferably the same as that of the visual flow indicators 138, 138' and 338 mentioned previously.

Figure 40:
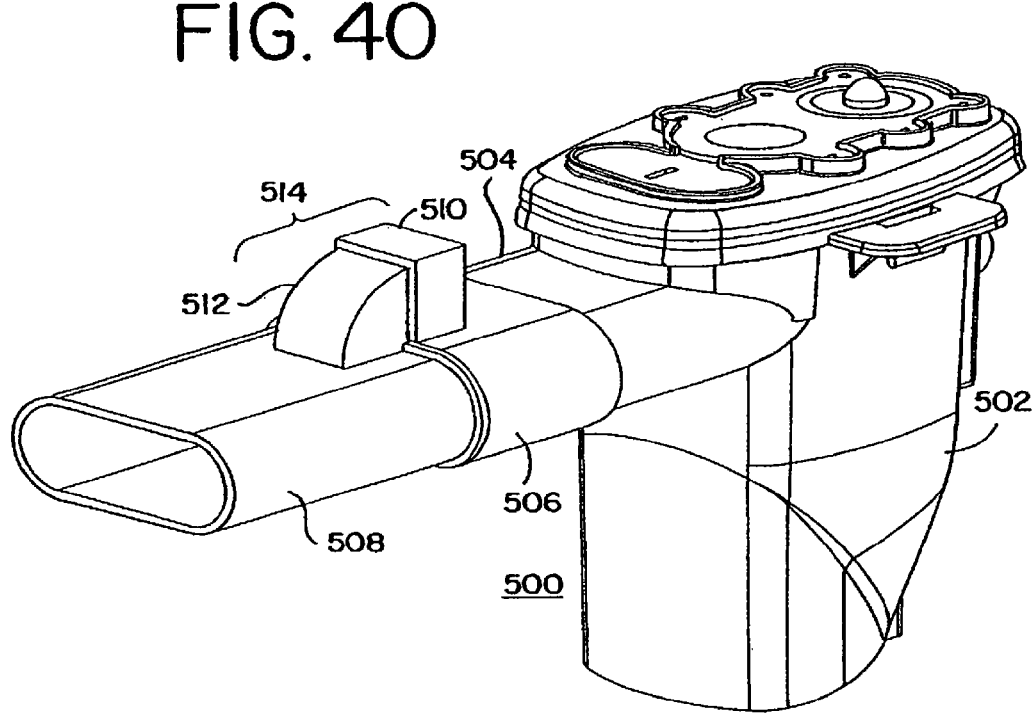
FIG. 40 shows a perspective view of an embodiment of a nebulizer delivery system according to the present invention.
Figure 41:
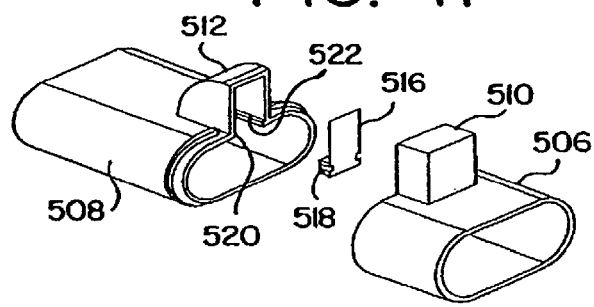
FIG. 41 shows a perspective, exploded view of an embodiment of a holding chamber and adapter according to the present invention to be used with the nebulizer delivery system of FIG. 40.
Figure 42:
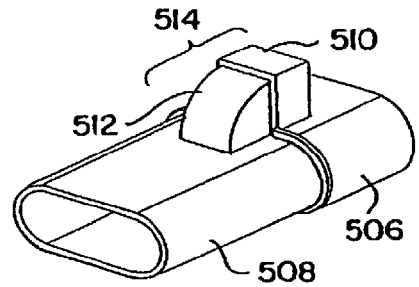
FIG. 42 shows a perspective view of the holding chamber and adapter of FIG. 41.

A visual flow indicator can also be used in nebulizer systems. A nebulizer 500 includes a chamber housing 502 that contains a liquid substance as shown in FIGS. 40-42. The chamber housing 502 is similar to the chamber housing disclosed in U.S. Pat. No. 5,823,179. The chamber housing 502 includes a rectangular-like exit port 504 that includes an opening (not shown). An interface includes an adapter 506 that is attached to the exit port 504 so as to be in fluid communication with the interior of the chamber housing 502. The interface also includes a mouthpiece 508 which is attached to the adapter 506 so that the mouthpiece 508 is in fluid communication with the interior of the chamber housing 502 via adapter 506. Attached to the adapter 506 and mouthpiece 508 are transparent housings 510, 512, respectively. When the mouthpiece 508 is attached to the adapter 506 a transparent viewing port area 514 is formed. Within the viewing port area 514, a visual flow indicator 516 is positioned. The visual flow indicator 516 has a pair of lower slots 518 that receive a pair of ridges 520, 522 formed within the mouthpiece 508. Once the ridges 520, 522 are received in the slots 518, the visual flow indicator 516 is permanently attached to the ridges 520, 522 by using an adhesive.

In operation, the patient activates the storage unit 502 by inhaling through the mouthpiece 508. Upon inhalation, the liquid within the housing 502 is introduced by the opening (not shown) of the exit port 504 to a downstream path along which the substance travels through the interface and the mouthpiece 508 to reach the patient. Thus, the interface 506 and mouthpiece 508 each operate as conduits for the inhaled substance. During inhalation the upper part of the visual flow indicator 516 will pivot downward to a horizontal position. If the patient is not inhaling or fails to inhale above a specified rate of inhalation, the upper part of the visual flow indicator 516 will remains in a vertical position blocking an opening of the housing 510. The range of motion of the visual flow indicator 516 is preferably the same as that of the visual flow indicators 138, 138', 338 and 412 mentioned previously.

As described previously, a visual flow indicator according to the present invention can be used in a variety of aerosol delivery systems. In each of the described systems, there is a common way to explain the present invention to encompass each of the previously described aerosol delivery systems. In particular, the aerosol delivery systems can each be thought of as containing a flow indicating system where the portion of the delivery system, such as an interface or a chamber housing, that is attached to the view port area is deemed a conduit. The conduit defines an interior space along which a substance, such as an aerosolized medication, primarily flows along a flow path defined within the interior space. The flow indicating mechanism includes a flow indicator, such as the flow indicators described in FIGS. 1-42, that is positioned within the conduit so as to be viewed via the viewing port, but is positioned substantially outside of the flow path so as to not to substantially interfere with the flow of the substance along the interior space.

The embodiments of the invention disclosed herein are presently considered to be preferred, various changes and modifications can be made without departing from the spirit and scope of the invention. As noted, the discussion above is descriptive, illustrative and exemplary and is not to be taken as limiting the scope defined by any appended claims, and all changes that come within the meaning and range of equivalents are intended to be embraced therein.

We claim:

1. A medication delivery system comprising:
a chamber housing comprising an exit port;
a patient interface releasably coupled to the chamber housing and comprising a mouthpiece defining an inhalation conduit and defining an opening positioned above the inhalation conduit;
a flow control member comprising a flap having a free end and an anchor portion formed along an end of the flap opposite the free end, wherein the flow control member is slideable from a non-engaged position, wherein the anchor portion is disengaged from the mouthpiece, to an engaged position, wherein the anchor portion is engaged with the mouthpiece and wherein the flap covers the opening, wherein the patient interface and flow control member define a self-contained unit when the flow control member is in the engaged position, wherein the self-contained unit is moveable between a disengaged position such that the self-contained unit is decoupled from the chamber housing, to an engaged position such that the self-contained unit is coupled to the chamber housing.

2. The medication delivery system of claim 1 wherein the anchor portion comprises a groove, and the mouthpiece comprises a ridge, wherein the ridge is received in the groove as the flow control member is slid to the engaged position.

3. The medication delivery system of claim 2 wherein the groove extends across a width of the anchor portion.

4. The medication delivery system of claim 1 wherein the anchor portion engages the mouthpiece with a snap-fit in the engaged position.

5. The medication delivery system of claim 1 wherein the free end of the flap is configured with a rounded edge.

6. The medication delivery system of claim 5 wherein the free end has a semi-circular shape.

7. A method for assembling a medication delivery system comprising:
providing a chamber housing comprising an exit port;
providing a patient interface comprising a mouthpiece defining an inhalation conduit and defining an opening positioned above the inhalation conduit;
providing a flow control member comprising a flap having a free end and an anchor portion formed along an end of the flap opposite the free end;
sliding the flow control member relative to the mouthpiece from a non-engaged position, wherein the anchor portion is disengaged from the mouthpiece, to an engaged position, wherein the anchor portion is engaged with the mouthpiece and wherein the flap covers the opening, wherein the patient interface and flow control member define a self-contained unit when the flow control member is in the engaged position; and
releasably coupling the self-contained unit to the chamber housing.

8. The method of claim 7 wherein sliding the flow control member from the non-engaged position to the engaged position comprises engaging a ridge formed on the mouthpiece with a groove formed on the anchor portion.

9. The method of claim 8 wherein the groove extends across a width of the anchor portion.

10. The method of claim 7 wherein sliding the flow control member from the non-engaged position to the engaged position comprises engaging the mouthpiece with the anchor portion by way of a snap-fit.

11. The method of claim 7 wherein the free end of the flap is configured with a rounded edge.

12. The method of claim 11 wherein the free end has a semi-circular shape.

13. A medication delivery system comprising:
a chamber housing comprising an exit port;
a patient interface coupled to the chamber housing and comprising a mouthpiece defining an inhalation conduit and defining a first opening positioned above the inhalation conduit;
a first flow control member disposed in the inhalation conduit;
a port coupled to the mouthpiece and disposed above the inhalation conduit, the port having a front portion communicating with the first opening, a rear portion having a second opening communicating with the ambient environment, and a stop disposed in the port between the first and second openings, the stop defining a third opening in the port, wherein the second opening is spaced apart from the first opening, and the third opening is spaced apart from the second opening; and
a second flow control member separate from the first flow control member and disposed in the port, wherein the second flow control member comprises a flap having a free end and an anchor portion formed along an end of the flap opposite the free end, the anchor portion non-moveably secured to the port, wherein the flap of the second flow control member is moveable within the port in response to a breathing cycle of a user, and wherein the flap of the second flow control member is biased toward the stop and covers the third opening in an at-rest position.

14. The medication delivery system of claim 13 wherein the stop has a vertical orientation.

15. The medication delivery system of claim 14 wherein the flap of the second flow control member is vertically oriented when in the at-rest position.

16. The medication delivery system of claim 13 wherein the third opening is circular.

17. The medication delivery system of claim 13 wherein the first flow control member is configured as a duckbill valve.

18. The medication delivery system of claim 13 wherein at least the front portion of the port is integrally formed with the patient interface.

19. The medication delivery system of claim 18 wherein the first opening is further defined by a bottom of the front portion at a location spaced apart from the stop.

20. The medication delivery system of claim 13 wherein the front and rear portions are configured as separate front and rear housings, wherein the rear housing is coupled to the front housing.

21. The medication delivery system of claim 13 wherein the rear portion of the port overlies a portion of the chamber housing spaced rearwardly from the exit port.

22. The medication delivery system of claim 21 wherein the second opening is spaced rearwardly from the exit port.

23. The medication delivery system of claim 13 wherein the front portion comprises a curved front wall facing a user when in use.

24. The medication delivery system of claim 13 wherein at least a portion of the port is transparent.

25. The medication delivery system of claim 13 wherein the free end of the flap is configured with a rounded edge.

26. The medication delivery system of claim 25 wherein the free end has a semi-circular shape.

27. The medication delivery system of claim 13 wherein the port is raised radially outwardly from an outer surface of the mouthpiece along only an upper portion of the mouthpiece.

* * * * *